(12) United States Patent
Reinke et al.

(10) Patent No.: US 9,808,632 B2
(45) Date of Patent: Nov. 7, 2017

(54) IMPLANTABLE MEDICAL DEVICE WITH DUAL-USE COMMUNICATION MODULE

(71) Applicant: Medtronic, Inc., Minneapolis, MN (US)

(72) Inventors: James D. Reinke, Maple Grove, MN (US); James K. Carney, Roseville, MN (US); Can Cinbis, Salt Lake City, UT (US); David J. Peichel, Minneapolis, MN (US); Joseph Ballis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/603,733

(22) Filed: Jan. 23, 2015

(65) Prior Publication Data

US 2016/0213937 A1    Jul. 28, 2016

(51) Int. Cl.
*A61N 1/372*    (2006.01)
*A61N 1/375*    (2006.01)
(Continued)

(52) U.S. Cl.
CPC ........ *A61N 1/37288* (2013.01); *A61B 5/0452* (2013.01); *A61B 5/6846* (2013.01);
(Continued)

(58) Field of Classification Search
CPC ...... A61N 1/025; A61N 1/0504; A61N 1/056; A61N 1/0565; A61N 1/0587; A61N 1/362;
(Continued)

(56) References Cited

U.S. PATENT DOCUMENTS 3,967,202 A    6/1976 Batz
4,987,897 A    1/1991 Funke
(Continued)

FOREIGN PATENT DOCUMENTS

EP    2441491 A1    4/2012
WO    2010042750 A2    4/2010
(Continued)

OTHER PUBLICATIONS

Wikipedia, "Radio Spectrum", <https://en.wikipedia.org/wiki/Radio_spectrum>. Accessed Jul. 26, 2016.*
(Continued)

*Primary Examiner* — Eugene T Wu

(57) ABSTRACT

An implantable medical device comprises a communication module that comprises at least one of a receiver module and a transmitter module. The receiver module is configured to both receive from an antenna and demodulate an RF telemetry signal, and receive from a plurality of electrodes and demodulate a tissue conduction communication (TCC) signal. The transmitter module is configured to modulate and transmit both an RF telemetry signal via the antenna and a TCC signal via the plurality of electrodes. The RF telemetry signal and the TCC signal are both within a predetermined band for RF telemetry communication. In some examples, the IMD comprises a switching module configured to selectively couple one of the plurality of electrodes and the antenna to the receiver module or transmitter module.

27 Claims, 7 Drawing Sheets

(51) Int. Cl.
*A61N 1/39* (2006.01)
*A61N 1/362* (2006.01)
*A61N 1/365* (2006.01)
*A61B 5/0452* (2006.01)
*A61B 5/00* (2006.01)
*A61N 1/05* (2006.01)

(52) U.S. Cl.
CPC ............ *A61N 1/365* (2013.01); *A61N 1/3621* (2013.01); *A61N 1/3756* (2013.01); *A61N 1/37229* (2013.01); *A61N 1/37252* (2013.01); *A61N 1/3956* (2013.01); *A61N 1/3962* (2013.01); *A61N 1/0534* (2013.01); *A61N 1/3622* (2013.01); *A61N 1/3627* (2013.01); *A61N 1/37205* (2013.01); *A61N 1/37217* (2013.01)

(58) Field of Classification Search
CPC .... A61N 1/3621; A61N 1/3622; A61N 1/368; A61N 1/37205; A61N 1/37211; A61N 1/37217; A61N 1/37223; A61N 1/37252; A61N 1/37276; A61N 1/37288; A61N 1/3956; A61N 1/3962; A61N 1/3756
See application file for complete search history.

(56) References Cited

U.S. PATENT DOCUMENTS

| | | | |
|---|---|---|---|
| 5,107,833 A | 4/1992 | Barsness | |
| 5,113,859 A | 5/1992 | Funke | |
| 5,117,824 A | 6/1992 | Keimel et al. | |
| 5,545,186 A | 8/1996 | Olson et al. | |
| 5,755,736 A | 5/1998 | Gillberg et al. | |
| 6,115,636 A | 9/2000 | Ryan | |
| 6,201,993 B1 | 3/2001 | Kruse et al. | |
| 6,788,973 B2 | 9/2004 | Davis et al. | |
| 6,847,298 B2 | 1/2005 | Lunenburg et al. | |
| 7,630,767 B1 * | 12/2009 | Poore | A61N 1/3627 607/32 |
| 7,991,467 B2 | 8/2011 | Markowitz et al. | |
| 8,083,674 B2 | 12/2011 | Such et al. | |
| 8,258,962 B2 | 9/2012 | Robertson et al. | |
| 8,412,352 B2 | 4/2013 | Griswold et al. | |
| 8,457,742 B2 | 6/2013 | Jacobson | |
| 8,515,559 B2 | 8/2013 | Roberts et al. | |
| 8,540,633 B2 | 9/2013 | Hafezi et al. | |
| 8,543,190 B2 | 9/2013 | Wasson et al. | |
| 8,547,248 B2 * | 10/2013 | Zdeblick | A61B 5/0028 340/870.28 |
| 8,744,572 B1 | 6/2014 | Greenhut et al. | |
| 8,798,205 B2 | 8/2014 | Ecker et al. | |
| 2006/0085041 A1 | 4/2006 | Hastings et al. | |
| 2006/0136004 A1 * | 6/2006 | Cowan | A61N 1/37205 607/33 |
| 2007/0088394 A1 * | 4/2007 | Jacobson | A61N 1/3925 607/4 |
| 2008/0071328 A1 | 3/2008 | Haubrich et al. | |
| 2011/0160557 A1 * | 6/2011 | Cinbis | A61B 5/0028 600/374 |
| 2011/0160801 A1 | 6/2011 | Markowitz et al. | |
| 2012/0081201 A1 | 4/2012 | Norgaard et al. | |
| 2012/0109236 A1 | 5/2012 | Jacobson et al. | |
| 2013/0116529 A1 * | 5/2013 | Min | A61B 5/042 600/375 |
| 2013/0211470 A1 * | 8/2013 | Benecke | A61N 1/37217 607/5 |
| 2013/0253345 A1 | 9/2013 | Griswold et al. | |
| 2014/0277286 A1 * | 9/2014 | Cinbis | A61N 1/37276 607/60 |
| 2015/0174414 A1 * | 6/2015 | Stahmann | A61N 1/3708 607/4 |
| 2015/0196756 A1 * | 7/2015 | Stahmann | A61N 1/3962 607/4 |
| 2015/0360036 A1 * | 12/2015 | Kane | A61N 1/36585 607/18 |
| 2016/0213939 A1 | 7/2016 | Carney et al. | |

FOREIGN PATENT DOCUMENTS

| | | |
|---|---|---|
| WO | 2010051385 A1 | 5/2010 |
| WO | 2012057861 A1 | 5/2012 |
| WO | 2013080038 A2 | 6/2013 |

OTHER PUBLICATIONS (PCT/US2016/014499) PCT Notification of Transmittal of the International Search Report and the Written Opinion of the International Searching Authority, dated Apr. 25, 2016, 12 pages.

* cited by examiner

IMPLANTABLE MEDICAL DEVICE WITH DUAL-USE COMMUNICATION MODULE

TECHNICAL FIELD

The disclosure relates to medical devices and, more particularly, to communication between implantable medical devices.

BACKGROUND

A wide variety of implantable medical devices (IMDs) for delivering a therapy or monitoring a physiological condition have been used clinically or proposed for clinical use in patients. Examples include IMDs that deliver therapy to and/or monitor conditions associated with the heart, muscle, nerve, brain, stomach or other tissue. Some therapies include the delivery of electrical stimulation to such tissues. Some IMDs may employ electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Implantable cardioverter defibrillators, for example, may be used to deliver high energy anti-tachyarrhythmia shocks, e.g., defibrillation shocks and/or cardioversion shocks, to a patient's heart when atrial or ventricular tachyarrhythmia, e.g., tachycardia or fibrillation, is detected. An implantable cardioverter defibrillator (ICD) may detect a tachyarrhythmia based on an analysis of a cardiac electrogram sensed via electrodes, and may deliver anti-tachyarrhythmia shocks via electrodes. An implantable cardiac pacemaker, as another example, may provide cardiac pacing therapy to the heart when the natural pacemaker and/or conduction system of the heart fails to provide synchronized atrial and ventricular contractions at rates and intervals sufficient to sustain healthy patient function. Implantable cardiac pacemakers may also provide overdrive cardiac pacing, referred to as anti-tachycardia pacing (ATP), to suppress or convert detected tachyarrhythmias. Implanted cardiac pacemakers may sense a cardiac electrogram and deliver cardiac pacing pulses via electrodes.

Some IMDs are coupled to one or more of the electrodes used to sense electrical physiological signals and deliver electrical stimulation via one or more leads, which allow the IMD housing to be positioned a desired distance from the target site for sensing or stimulation delivery. For example, a subcutaneously or sub-muscularly implanted housing of an ICD or implantable cardiac pacemaker may be coupled to endocardial electrodes via leads. Other ICDs, referred to as extravascular ICDs, are not coupled to any endocardial electrodes, and instead sense and deliver shocks via a plurality of electrodes, e.g., implanted subcutaneously or substernally, which may be provided by the housing of the subcutaneous ICD and/or coupled to the housing via one or more leads.

Leadless IMDs may also be used to deliver therapy to a patient, and/or sense physiological parameters of a patient. In some examples, a leadless IMD may include one or more electrodes on its outer housing to deliver therapeutic electrical stimulation to patient, and/or sense intrinsic electrical signals of patient. For example, a leadless pacing device (LPD) may be used to sense intrinsic depolarizations or other physiological parameters of the heart, and/or deliver therapeutic electrical stimulation to the heart. LPDs may be positioned within or outside of the heart and, in some examples, may be anchored to a wall of the heart via a fixation mechanism.

In some situations, two or more IMDs are implanted within a single patient. For example, as an alternative to an ICD with cardiac pacing capabilities coupled to endocardial electrodes via transvenous leads, it has been proposed to implant an extravascular ICD capable of delivering anti-tachyarrhythmia shocks, and a separate LPD capable of providing cardiac pacing. In some situations, it may be desirable for the two or more IMDs to be able to communicate with each other, e.g., to coordinate, or cooperatively provide, sensing and/or therapy delivery. For example, it may be desirable to allow an extravascular ICD and LPD to communicate to coordinate delivery of ATP and anti-tachyarrhythmia shocks in response to a tachyarrhythmia detected by one or both of the IMDs. Although some IMDs communicate with external devices, e.g., programming devices, using radio-frequency (RF) telemetry, it has also been proposed to use tissue conduction communication (TCC) for communication between an IMD and an external device, or between an IMD and another IMD.

SUMMARY

Generally, this disclosure describes various techniques for facilitating tissue conduction communication (TCC) between an implantable medical device (IMD) and another device, such as another IMD. More particularly, this disclosure describes techniques for transmitting and/or receiving radio-frequency (RF) telemetry signals and TCC signals using a common communication module of an IMD that is configured to modulate and transmit, and/or receive and demodulate, signals within a common predetermined frequency band for RF telemetry communication and TCC. In some examples, an IMD comprises a communication module that comprises at least one of a receiver module and a transmitter module. The receiver module is configured to both receive from the antenna and demodulate an RF telemetry signal, and receive from the plurality of electrodes and demodulate a TCC signal. The transmitter module is configured to modulate and transmit both an RF telemetry signal via the antenna and a TCC signal via the plurality of electrodes. The RF telemetry signal and the TCC signal are both within a predetermined frequency band for RF telemetry communication.

In some examples, the IMD comprises a switching module configured to selectively couple either the plurality of electrodes or the antenna to the at least one of the receiver module or the transmitter module. In some examples, the IMD senses a physiological signal and/or delivers therapeutic signals via at least one electrode of the plurality of electrodes. In such examples, the switching module may be configured to selectively couple the at least one electrode to a sensing module for sensing the physiological signal, a therapeutic signal generator for delivering the therapeutic signals, or the at least one of the receiver module or the transmitter module.

A communication module configured to transmit and/or receive both RF telemetry signals and TCC signals, according to the techniques described in this disclosure, may take up less space within a housing of the IMD than separate communication modules configured to transmit and/or receive RF telemetry signals and TCC signals, respectively. Consequently, such a communication module may facilitate a relatively smaller IMD housing. A smaller IMD housing may be particularly advantageous for configuration of IMDs for implantation in relatively confined locations, such as configuration of a leadless pacing device (LPD) for implantation within a cardiac chamber, configuration of an implantable pressure sensor within a cardiac chamber or blood vessel, or configuration of an implantable neurostimulator within the pelvic floor, as well as relative ease in navigation of the IMD to its final implant location via transcatheter implant techniques.

In some examples, an LPD comprises a communication receiver module configured to demodulate both RF telemetry and TCC signals, received via an antenna and a plurality of electrodes, respectively. The receiver module of the LPD may receive and demodulate a TCC signal from a co-implanted extravascular ICD. The TCC signal may include a command to deliver anti-tachycardia pacing (ATP) or post-shock pacing. In some examples, the extravascular ICD includes a communication transmitter module configured to modulate and deliver both RF telemetry signals and TCC signals, such as the TCC signal including the ATP or post-shock pacing command, via an antenna and a plurality of electrodes, respectively. In some examples, a communication module of the LPD and/or the extravascular ICD includes both a transmitter module and a receiver module configured to implement the techniques of this disclosure.

In one example, the disclosure describes an implantable medical device configured for implantation in a patient comprising an antenna, a plurality of electrodes, and a communication module. The communication module comprises at least one of a communication receiver module and a communication transmitter module. The communication receiver module is configured to receive and demodulate signals within a predetermined frequency band for RF telemetry communication. The communication receiver module is configured to receive from the antenna and demodulate a first RF telemetry signal emitted by an external device outside of the patient, and receive from the plurality of electrodes and demodulate a first tissue conductance communication (TCC) signal emitted by another implantable medical device implanted within the patient. The first RF telemetry signal and the first TCC signal are within the predetermined band for RF telemetry communication. The communication transmitter module is configured to modulate and transmit signals within the predetermined frequency band for RF telemetry communication. The communication transmitter module is configured to modulate and transmit a second RF telemetry signal to the external device via the antenna, and modulate and transmit a second TCC signal to the other implantable medical device via the plurality of electrodes. The second RF telemetry signal and the second TCC signal are within the predetermined band for RF telemetry communication.

In another example, the disclosure describes a method for receiving and demodulating both radio-frequency (RF) telemetry signals and tissue conduction communication (TCC) signals with a common communication receiver module of an implantable medical device. The method comprises receiving, by the communication receiver module, an RF telemetry signal emitted by an external device outside of the patient via an antenna of the implantable medical device, wherein the RF telemetry signal is within a predetermined frequency band for RF telemetry communication, and demodulating, by the communication receiver module, the RF telemetry signal. The method further comprises receiving, by the communication receiver module, a TCC signal emitted by another implantable medical device implanted within the patient via a plurality of electrodes of the implantable medical device, wherein the TCC signal is within the predetermined frequency band for RF telemetry communication, and demodulating, by the communication receiver module, the TCC signal.

In another example, the disclosure describes a method for modulating and transmitting both radio-frequency (RF) telemetry signals and tissue conduction communication (TCC) signals with a common communication transmitter module of an implantable medical device. The method comprises modulating, by the communication transmitter module, an RF telemetry signal, and transmitting, by the communication transmitter module, the RF telemetry signal to an external device outside of the patient with an antenna of the implantable medical device, wherein the RF telemetry signal is within the predetermined frequency band for RF telemetry communication. The method further comprises modulating, by the communication transmitter module, a TCC signal, and transmitting, by the communication transmitter module, the TCC signal to another implantable medical device implanted within the patient with a plurality of electrodes of the implantable medical device, wherein the TCC signal is within the predetermined frequency band for RF telemetry communication.

In another example, the disclosure describes a system comprising an extravascular implantable cardioverter defibrillator and a leadless pacing device. The extravascular implantable cardioverter defibrillator comprises a first antenna, a first plurality of electrodes, a first sensing module configured to receive a first cardiac electrogram of the patient via the first plurality of electrodes, and a first therapeutic signal generator configured to deliver anti-tachyarrhythmia shocks to a heart of the patient via the first plurality of electrodes. The extravascular implantable cardioverter defibrillator further comprises a communication transmitter module configured to modulate and transmit signals within a predetermined frequency band for RF telemetry communication, wherein the communication transmitter module is configured to modulate and transmit a first RF telemetry signal to an external device via the first antenna, and modulate and transmit a tissue conductance communication (TCC) signal via the first plurality of electrodes, wherein the TCC signal is within the predetermined frequency band for RF telemetry communication. The extravascular implantable cardioverter defibrillator further comprises a first switching module configured to selectively couple the first plurality of electrodes to at least one of the first sensing module, the first therapeutic signal generator, or the first communication transmitter module. The leadless pacing device comprises a second antenna, a second plurality of electrodes, a second sensing module configured to receive a second cardiac electrogram of the patient via the second plurality of electrodes, and a second therapeutic signal generator configured to deliver cardiac pacing pulses to a heart of the patient via the second plurality of electrodes. The leadless pacing device further comprises a communication receiver module configured to receive and demodulate signals within the predetermined frequency band for RF telemetry communication, wherein the communication receiver module is configured to receive from the antenna and demodulate a second RF telemetry signal emitted by the external device, and receive from the second plurality of electrodes and demodulate the TCC signal emitted by the extravascular implantable cardioverter defibrillator. The leadless pacing device further comprises a second switching module configured to selectively couple the second plurality of electrodes to at least one of, the second sensing module, the second therapeutic signal generator, or the communication receiver module. The leadless pacing device further comprises a housing configured for implantation within the heart of the patient, wherein the housing encloses the second antenna, the communication receiver module, the second switching module, the second sensing module, and the second therapeutic signal generator, and wherein the housing comprises at least one of the second plurality of electrodes. The TCC signal includes a command from the extravascular implantable cardioverter defibrillator to the leadless pacing device to deliver at least one of anti-tachycardia pacing (ATP) or post-shock pacing.

The details of one or more examples are set forth in the accompanying drawings and the description below. Other features, objects, and advantages will be apparent from the description and drawings, and from the claims.

DETAILED DESCRIPTION

Figure 1:
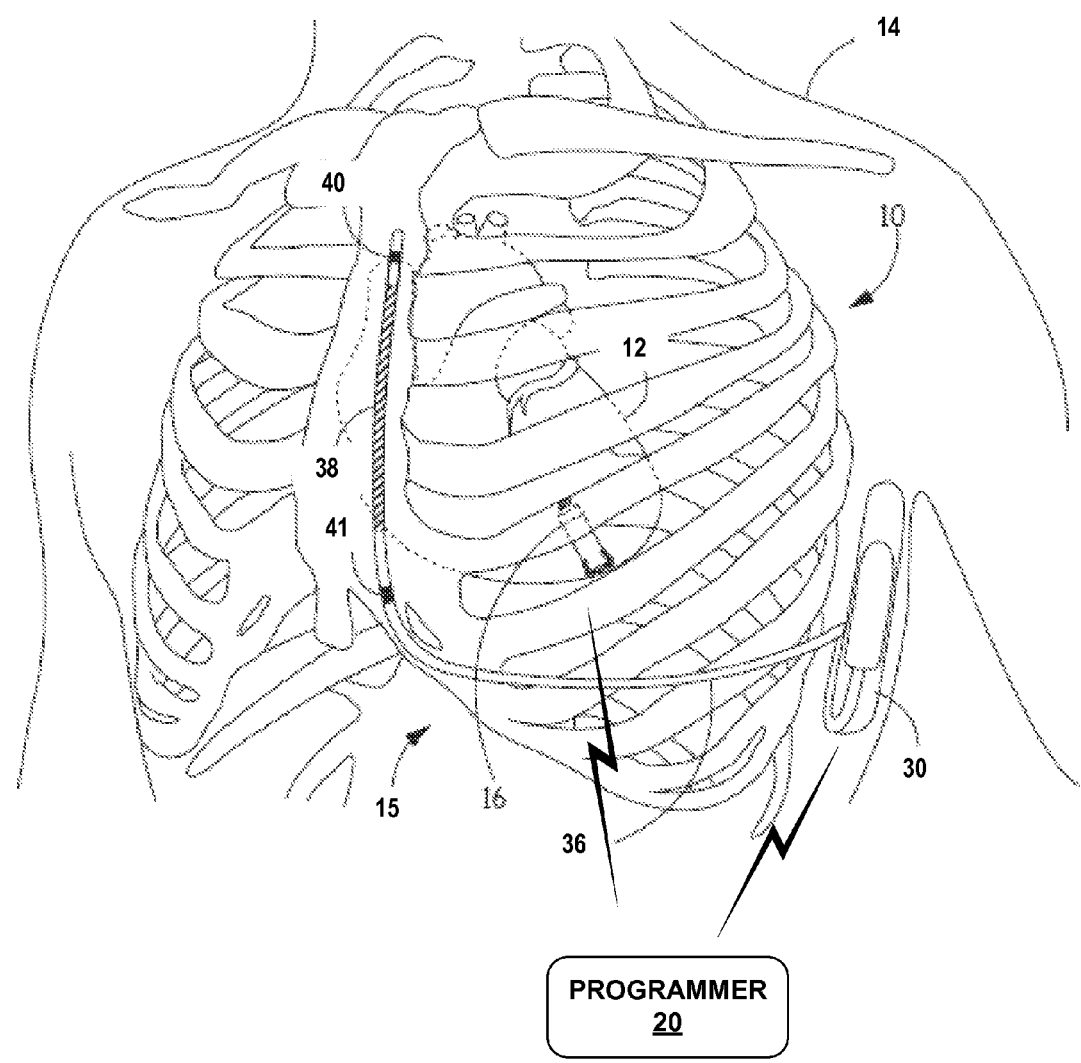
FIG. 1 is a conceptual drawing illustrating an example cardiac system that includes an extravascular implantable cardioverter defibrillator system implanted exterior to the rib cage of a patient and a leadless cardiac pacing device implanted within a heart of the patient.

FIG. 1 is a conceptual drawing illustrating an example cardiac system 10 implanted within a patient 14. Cardiac system 10 includes an extravascular implantable cardioverter defibrillator (ICD) system 15 implanted above the ribcage and sternum and a leadless pacing device (LPD) 16 implanted within a heart 12 of patient 14. ICD 30 of extravascular ICD system 15 and LPD 16 may communicate via tissue conductance communication (TCC). In some examples, the TCC communication may be "one-way" communication, e.g., from ICD 30 to LPD 16, or from LPD 16 to ICD 30. In some examples, the TCC communication may be "two-way" communication. As will be described in further detail herein, one or both of LPD 16 and ICD 30 may include a communication module configured to modulate and transmit, and/or receive and demodulate, radio-frequency (RF) telemetry signals within a predetermined frequency band for RF telemetry communication, as well as TCC signals within the predetermined frequency band for RF telemetry communication.

Extravascular ICD system 15 includes ICD 30 connected to at least one implantable cardiac defibrillation lead 36. ICD 30 of FIG. 1 is implanted subcutaneously on the left side of patient 14 under the skin but above the ribcage. Defibrillation lead 36 extends subcutaneously under the skin but above the ribcage from ICD 30 toward a center of the torso of patient 14, bends or turns near the center of the torso, and extends subcutaneously superior under the skin but above the ribcage and/or sternum. Defibrillation lead 36 may be offset laterally to the left or the right of the sternum or located over the sternum. Defibrillation lead 36 may extend substantially parallel to the sternum or be angled lateral from the sternum at either the proximal or distal end.

In other instances, lead 36 may be implanted at other extravascular locations. For example, lead 36 may be implanted at least partially in a substernal location, e.g., between the ribcage and/or sternum and heart. In one such configuration, a proximal portion of lead 36 extends subcutaneously from ICD 30 toward the sternum and a distal portion of lead 36 extends superior under or below the sternum in the anterior mediastinum. The anterior mediastinum is bounded laterally by the pleurae, posteriorly by the pericardium, and anteriorly by the sternum. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 36 extends along the posterior side of the sternum substantially within the loose connective tissue and/or substernal musculature of the anterior mediastinum. Lead 36 may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum or ribcage.

Defibrillation lead 36 includes a defibrillation electrode 38 toward the distal portion of defibrillation lead 36, e.g., toward the portion of defibrillation lead 36 extending along the sternum. Defibrillation lead 36 is placed along sternum such that a therapy vector between defibrillation electrode 38 and a housing electrode formed by or on ICD 30 (or other second electrode of the therapy vector) is substantially across a ventricle of heart 12. The therapy vector may, in one example, be viewed as a line that extends from a point on defibrillation electrode 38 (e.g., a center of the defibrillation electrode 38) to a point on the housing electrode of ICD 30. Defibrillation electrode 38 may, in one example, be an elongated coil electrode.

Defibrillation lead 36 may also include one or more sensing electrodes, such as sensing electrodes 40 and 41, located along the distal portion of defibrillation lead 36. In the example illustrated in FIG. 1, sensing electrodes 40 and 41 are separated from one another by defibrillation electrode 38. In other examples, however, sensing electrodes 40 and 41 may be both distal of defibrillation electrode 38 or both proximal of defibrillation electrode 38. In other examples, lead 36 may include more or fewer electrodes. Additionally, the exact configuration, shape, size, and implantation location of ICD 30 may be varied, e.g., from the examples depicted and described herein, for different applications or patients.

As described above, cardiac system 10 also includes at least one LPD 16. In the example illustrated in FIG. 1, LPD 16 provides pacing therapy to heart 18 via a pair of electrodes carried on the housing of pacing device 16. An example LPD is described in U.S. Pat. No. 8,744,572 to Greenhut et al., entitled "SYSTEMS AND METHODS FOR LEADLESS PACING AND SHOCK THERAPY," which issued on Jun. 3, 2014, the entire content of which is incorporated herein by reference. Since LPD 16 includes two or more electrodes carried on the exterior its housing, no other leads or structures need to reside in other chambers of heart 12.

In the example of FIG. 1, LPD 16 is implanted within right ventricle of heart 12 to sense electrical activity of heart 12 and deliver pacing therapy, e.g., ATP therapy, bradycardia pacing therapy, and/or post-shock pacing therapy, to heart 12. LPD 16 may be attached to a wall of the right ventricle of heart 12 via one or more fixation elements that penetrate the tissue. These fixation elements may secure LPD 16 to the cardiac tissue and retain an electrode (e.g., a cathode or an anode) in contact with the cardiac tissue. However, in other examples, system 10 may include additional LPDs 16 within respective chambers of heart 12 (e.g., right or left atrium and/or left ventricle). In further examples, LPD 16 may be attached to an external surface of heart 12 (e.g., in contact with the epicardium) such that LPD 16 is disposed outside of heart 12.

This disclosure describes various techniques for facilitating TCC between an implantable medical device (IMD) and another device, such as another IMD. In some situations, it may be desirable for the two or more IMDs to be able to communicate with each other, e.g., to coordinate, or cooperatively provide, sensing and/or therapy delivery. For example, it may be desirable to allow ICD 30 and LPD 16 to communicate to coordinate delivery of ATP therapy, anti-tachyarrhythmia shocks, and post-shock pacing in response to a tachyarrhythmia detected by one or both of the IMDs.

Extravascular ICD system 15 is configured to detect tachyarrhythmias and deliver anti-tachyarrhythmia shock therapy from one or more electrodes implanted subcutaneously, such as external to the ribcage of the patient. Extravascular ICD system 15 may thus deliver shocks to the patient without any leads implanted within the vasculature and/or heart of the patient. However, the absence of endocardial or epicardial electrodes may decrease the ability of extravascular ICD system 15 to provide, or the desirability of the extravascular ICD system providing, pacing therapy to the patient, such as ATP and post-shock pacing.

As discussed above, one or more LPDs 16 carrying one or more electrodes may be implanted within various chambers of the heart of the patient or otherwise in close proximity of the cardiac muscle. At such locations, LPD 16 may sense cardiac electrogram signals with high signal-to-noise ratios to detect arrhythmias. In addition, LPD 16 may provide cardiac pacing at the location of the implanted LPD. However, LPD 16 may not be capable of delivering an anti-tachyarrhythmia shock or sensing far-field cardiac electrogram signals indicative of global cardiac condition.

Extravascular ICD system 15 and one or more LPDs 16 may be co-implanted, as illustrated in the case of cardiac system 10 of FIG. 1, and ICD 30 and LPD 16 may communicate to enable a system level of functionality such as sharing the detection of arrhythmias between devices, synchronized timing of anti-tachyarrhythmia shocks, ATP, and/or post-shock pacing, and optimization of the resources (e.g., battery capacity or processing power) available to each device. In some examples, communication between the ICD 30 and LPD 16 may be used to initiate therapy and/or confirm that therapy should be delivered. One approach is for ICD 30 to function as the "master" and LPD 16 to function as the "slave" in a "master-slave" relationship. In such examples, LPD 16 would need to receive a signal from ICD 30 prior to delivering cardiac pacing therapy.

For example, ICD 30 may detect a tachyarrhythmia and determine to deliver an anti-tachyarrhythmia shocks to patient 14 to treat the tachyarrhythmia. In some examples, ICD 30 may be configured to, in response to the determination to deliver the shock, transmit a command or other communication requesting LPD 16 to deliver ATP. Delivery of ATP may be performed in an attempt to terminate the tachyarrhythmia prior to needing to deliver a shock. Since ICD 30 may require a period of time to charge prior to the ICD being capable of delivering the shock, the ATP may not delay the delivery of the shock.

In one example, ICD 30 may be configured to continually monitor electrical signals of heart 12 for tachyarrhythmias. ICD 30 may detect, based on a sensed electrical signal, a tachyarrhythmia eligible for anti-tachyarrhythmia shock therapy and/or ATP. In response to this detection, ICD 30 may a transmit communication to LPD 16 to deliver ATP. In such examples, ICD 30 may cause LPD 16 to "wake up" from an at least partially inactive state to an active state. LPD 16 may be set to inactive if it is not needed to treat conditions such as bradyarrhythmias in patient 14. However, if LPD 16 is required to monitor and/or treat bradyarrhythmias, LPD 16 may remain active to detect and/or treat tachyarrhythmias as well.

In addition to the delivery of ATP, LPD 16 may be configured to deliver post-shock pacing to heart 12. After delivery of an anti-tachyarrhythmia shock, heart 12 may benefit from pacing to return to a normal sinus rhythm, e.g., if heart 12 has developed bradycardia or asystole, or otherwise recover from receiving the shock. In some examples, LPD 16 and/or ICD 30 may be configured to detect bradycardia or asystole, e.g., after delivery of a shock to terminate a tachyarrhythmia. In some examples, this post-shock pacing therapy may be automatically delivered by LPD 16 in response to detecting a shock, or the resulting bradycardia or asystole. In some examples, after ICD 30 delivers one or more shocks, ICD 30 may transmit a command to LPD 16 instructing LPD 16 to deliver post-shock pacing, e.g., in response to determining that a delivered shock terminated a tachyarrhythmia or detecting bradycardia or asystole resulting from a delivered shock.

In some examples, LPD 16 may transmit a communication message to ICD 30. For example, LPD 16 may first detect, or in response to a query from ICD 30 confirm, a tachyarrhythmia eligible for an anti-tachyarrhythmia shock and/or ATP therapy. In some examples, LPD 16 may command the ICD 30 to deliver one or more shocks in response to a tachyarrhythmia detected by LPD 16.

Because there are no wires connecting ICD 30 to LPD 16, ICD 30 and LPD 16 may use a wireless communication technique to remain synchronized and prevent device-to-device interference. Wireless techniques for IMD communication include RF telemetry, inductive telemetry, acoustics, and TCC. During TCC, current is driven through the tissue between two or more electrodes of the transmitting IMD (or external device), e.g., between two or more of defibrillation electrode 38, an electrode formed on or by the housing of ICD 30, sensing electrode 40, or sensing electrode 41 of extravascular ICD system 15. The current spreads through the thorax, producing a potential field. The receiving IMD (or external device) may detect the TCC signal by measuring the potential difference between two of its electrodes, e.g., the pacing tip and sense ring of LPD 16.

TCC may be a desired technique for inter-IMD communication. However, many IMDs already include circuitry for RF telemetry communication with external devices, such as programming devices. In general, it may be desirable for an IMD to be as small as possible; particularly IMDs configured for implantation in relatively confined locations, such as configuration of LPD 16 for implantation within a cardiac chamber. Therefore, the size of the circuitry and components within a housing of the IMD should be constrained to the extent possible. Additionally, the power required by such circuitry and components should be constrained to the extent possible.

LPD 16 and ICD 30 include a communication module configured to receive and demodulate, and modulate and transmit, signals within a predetermined frequency band for RF telemetry communication. The communication module includes a receiver module configured to receive RF telemetry signals, e.g., from external programmer 20, via an antenna of the IMD, and demodulate the RF telemetry signals. The communication module also includes a transmitter module configured to modulate RF telemetry signals, and transmit the RF telemetry signals via the antenna, e.g., to external programmer 20. As an example, the predetermined frequency band for RF telemetry communication may be greater than or equal to approximately 100 kilohertz (kHz). As another example, the predetermined frequency band for RF telemetry communication may be within a range from approximately 150 kHz to approximately 200 kHz.

In some examples, the communication receiver module is also configured to receive TCC signals via a plurality of electrodes of the IMD, e.g., LPD 16 and/or ICD 30, and demodulate the TCC signals. The TCC signals are emitted by another device, e.g., another IMD, at a frequency within the predetermined frequency band for RF telemetry communication, e.g., greater than 100 kHz. In some examples, the communication transmitter module is also configured to modulate and transmit TCC signals via the plurality of electrodes of the IMD at a frequency within the predetermined frequency band for RF telemetry communication. Delivery of TCC signal pulses at or above 100 kHz may reduce the likelihood that the current will stimulate tissue, such as muscle or nerve tissue, or cause pain.

In some examples, LPD 16 and/or ICD 30 include a switching module. The switching module selectively couples the transmitter module or receiver module to either the antenna for RF telemetry communication or the electrodes for TCC. In some examples, the switching module may also selectively couple the electrodes to sensing and/or therapeutic signal generation circuitry.

A communication module configured to modulate and/or demodulate both RF telemetry signals and TCC signals, according to the techniques described in this disclosure, may take up less space within a housing of the IMD than separate communication modules configured for RF telemetry signals and TCC signals, respectively. Consequently, such a communication module may facilitate a relatively smaller IMD housing. A smaller IMD housing may be particularly advantageous for configuration of IMDs for implantation in relatively confined locations, such as configuration of LPD 16 for implantation within a cardiac chamber, configuration of an implantable pressure sensor within a cardiac chamber or blood vessel, or configuration of an implantable neurostimulator within the pelvic floor.

Although primarily described with respect to examples in which an ICD and LPD communicate to facilitate delivery of ATP and/or post-shock pacing, the techniques described in this disclosure may be implemented in other examples for other reasons and/or to facilitate communication between other coexistent systems. For example, the techniques of this disclosure may be implemented to facilitate TCC between an ICD and one or more LPDs, or between another IMD, such as a subcutaneously-implantable physiological monitor, and one or more LPDs, to facilitate delivery of cardiac resynchronization therapy (CRT) by the one or more LPDs. As another example, the techniques of this disclosure may be implemented to facilitate TCC between a plurality of LPDs, e.g., to coordinate delivery of cardiac pacing between different cardiac chambers, e.g., for CRT. As another example, the techniques of this disclosure may be implemented to facilitate TCC between any other IMD and an implantable neurostimulator, e.g., to control the timing of the neurostimulation. As another example, the techniques of this disclosure may be implemented to facilitate TCC between two IMDs that monitor physiological parameters, e.g., between an IMD that monitors an electrocardiogram and an IMD that monitors an electroencephalogram, to coordinate the content of timing of physiological measurements by the IMDs. In some examples, the techniques of this disclosure may be implemented to facilitate TCC between any IMDs, e.g., between one or more LPDs, ICDs, implantable cardiac pacemakers or implantable cardioverter defibrillators coupled to intracardiac electrodes, neurostimulators, pumps, or sensors, such as implantable pressure sensors. In some examples, the techniques of this disclosure may be implemented to facilitate TCC between any IMD and an external device, e.g., for programming the IMD, retrieving information from the IMD, or testing the ability of the IMD to communication via TCC, such as during implantation of the IMD. As such, the example of FIG. 1 is illustrated for exemplary purposes only and should not be considered limiting of the techniques described herein.

Figure 2:
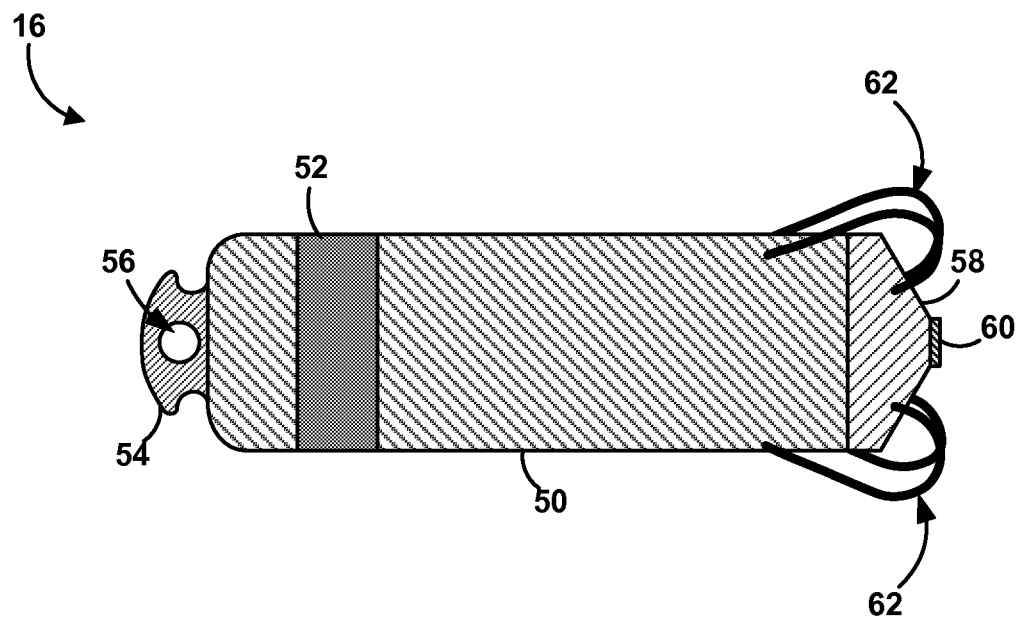
FIG. 2 is a conceptual drawing illustrating the example leadless pacing device of FIG. 1.

FIG. 2 is a conceptual drawing further illustrating LPD 16. As shown in FIG. 2, LPD 16 includes case 50, cap 58, electrode 60, electrode 52, fixation mechanisms 62, flange 54, and opening 56. Together, case 50 and cap 58 may be considered the housing of LPD 16. In this manner, case 50 and cap 58 may enclose and protect the various electrical components within LPD 16. Case 50 may enclose substantially all of the electrical components, and cap 58 may seal case 50 and create the hermetically sealed housing of LPD 16. Although LPD 16 is generally described as including two electrodes 52 and 60, LPD 16 may typically include two or more electrodes to deliver an electrical signal (e.g., therapeutic signals such as pacing pulses and/or a TCC signal) and/or provide at least one sensing vector for sensing a cardiac electrogram and/or a TCC signal.

Electrodes 52 and 60 are carried on the housing created by case 50 and cap 58. In this manner, electrodes 52 and 60 may be considered leadless electrodes. In the example of FIG. 2, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating.

Electrode 60 may be used as a cathode and electrode 52 may be used as an anode, or vis-a-versa, for cardiac pacing therapy, such as ATP or post-shock pacing, or transmitting TCC signals. In addition, electrodes 52 and 60 may be used to detect intrinsic electrical signals from cardiac muscle. In other examples, LPD 16 may include three or more electrodes, where any two or more of the electrodes may form a vector for delivery of therapy, detecting intrinsic signals, transmitting TCC signals, and receiving TCC signals. In some examples in which LPD 16 includes three or more electrodes, the LPD may select two or more of the electrodes, e.g., via switches, to form a vector for TCC. LPD 16 may use multiple vectors for TCC to, for example, provide signal or vector diversity, which may improve the quality or reliability of TCC.

Fixation mechanisms 62 may attach LPD 16 to cardiac tissue. Fixation mechanisms 62 may be active fixation tines, screws, clamps, adhesive members, or any other types of attaching a device to tissue. As shown in the example of FIG. 2, fixation mechanisms 62 may be constructed of a shape memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of LPD 16. For example, a suture or other device may be inserted around flange 54 and/or through opening 56 and attached to tissue. In this manner, flange 54 may provide a secondary attachment structure to tether or retain LPD 16 within heart 12 if fixation mechanisms 62 fail. Flange 54 and/or opening 56 may also be used to extract LPD 16 once the LPD needs to be explanted (or removed) from patient 14 if such action is deemed necessary.

Figure 3:
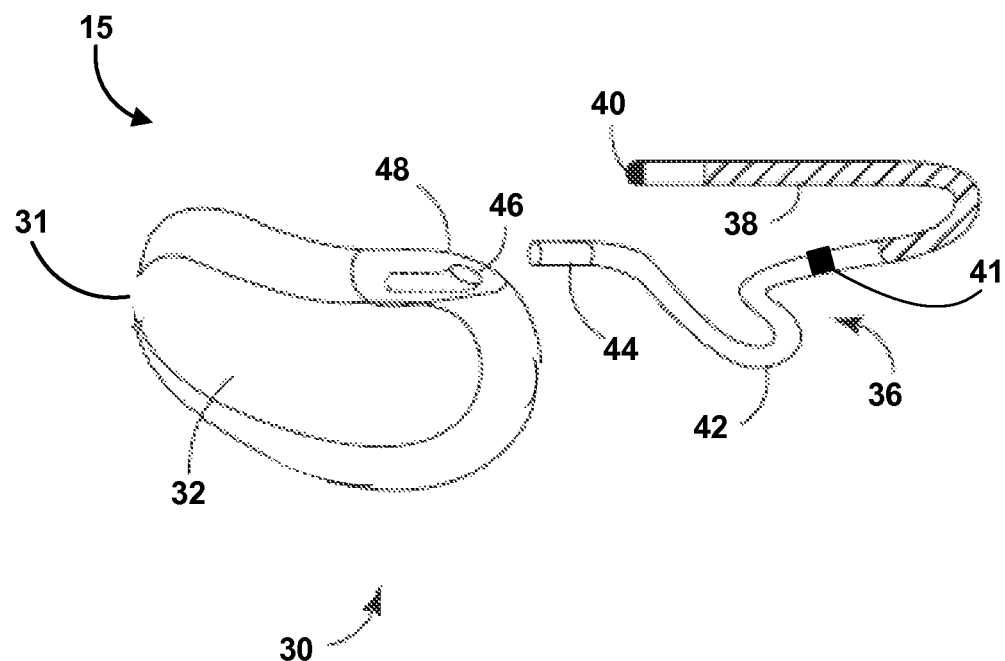
FIG. 3 is a conceptual drawing illustrating the example extravascular implantable cardioverter defibrillator system of FIG. 1

FIG. 3 is a conceptual drawing further illustrating ICD 30 of FIG. 1. In the example of FIG. 3, housing 31 may be constructed as an ovoid with a substantially kidney-shaped profile. The ovoid shape of housing 31 may promote ease of subcutaneous implantation and may minimize patient discomfort during normal body movement and flexing of the thoracic musculature. In other examples, housing 31 may be constructed with different shapes intended for different implant locations and/or to house different components, or to be coupled to different subcutaneous leads.

Housing 31 may contain the electronic circuitry of ICD 30. Defibrillation lead 36 may include distal defibrillation coil electrode 38, distal sensing electrode 40, proximal sensing electrode 41, insulated flexible lead body 42 and proximal connector pin 44. Proximal connector pin 44 of lead 36 may be inserted into connector 46 of header 48. Header 48 and connector 46 of ICD 30, and connector pin 44 at a proximal end of defibrillation lead 36, may provide electrical connections between electrodes 38, 40, and 41 of lead 36, and the circuitry within housing 31 of ICD 30. Defibrillation lead 36 includes one or more conductors that form an electrically conductive path within the lead body and interconnect the electrical connections and respective ones of the electrodes. In some examples, housing 31, or a portion thereof, may be configured as an electrically conductive surface and operate as an electrode 32, e.g., a can or housing electrode 32, for delivery of electrical signals and/or sensing.

ICD 30 may sense intrinsic electrical signals, e.g., a cardiac electrogram, from one or more sensing vectors formed by two or more of electrodes 32, 38, 40 and 41, such as one or more sensing vectors that include combinations of electrodes 40 and 41 and housing electrode 32. For example, ICD 30 may obtain electrical signals sensed using a sensing vector between electrodes 40 and 41, obtain electrical signals sensed using a sensing vector between electrode 40 and housing electrode 32 of ICD 30, obtain electrical signals sensed using a sensing vector between electrode 41 and housing electrode 32 of ICD 30, or a combination thereof. In some instances, ICD 30 may even sense cardiac electrical signals using a sensing vector that includes defibrillation electrode 38 and one of electrodes 40 and 41 or housing electrode 32 of ICD 30.

The sensed electrical intrinsic signals may include electrical signals generated by cardiac muscle and indicative of depolarizations and repolarizations of heart 12 at various times during the cardiac cycle. Additionally, the sensed electrical signals may also include electrical signals, e.g., pacing pulses, generated and delivered to heart 12 by LPD 16. ICD 30 analyzes the electrical signals sensed by the one or more sensing vectors to detect tachyarrhythmia, such as ventricular tachycardia or ventricular fibrillation. In response to detecting the tachyarrhythmia, ICD 30 may begin to charge a storage element, such as a bank of one or more capacitors, and, when charged, deliver one or more anti-tachyarrhythmia shocks via defibrillation electrode 38 of defibrillation lead 36 if the tachyarrhythmia is still present and determined to require anti-tachyarrhythmia shock therapy.

ICD 30 may also sense TCC signals via a vector formed by two or more of electrodes 32, 38, 40 and 41. ICD 30 may also deliver therapeutic shocks via a vector formed by two or more of the electrodes, such as subcutaneous electrode 38 and housing electrode 32. ICD 30 may also transmit TCC signals via a vector formed by two or more of the electrodes, such as electrode 38 and housing electrode 32. In some examples, ICD 30 may select two or more of the electrodes, e.g., via switches, to form a vector for TCC. ICD 30 may use multiple vectors for TCC to, for example, provide signal or vector diversity, which may improve the quality or reliability of TCC.

Figure 4:
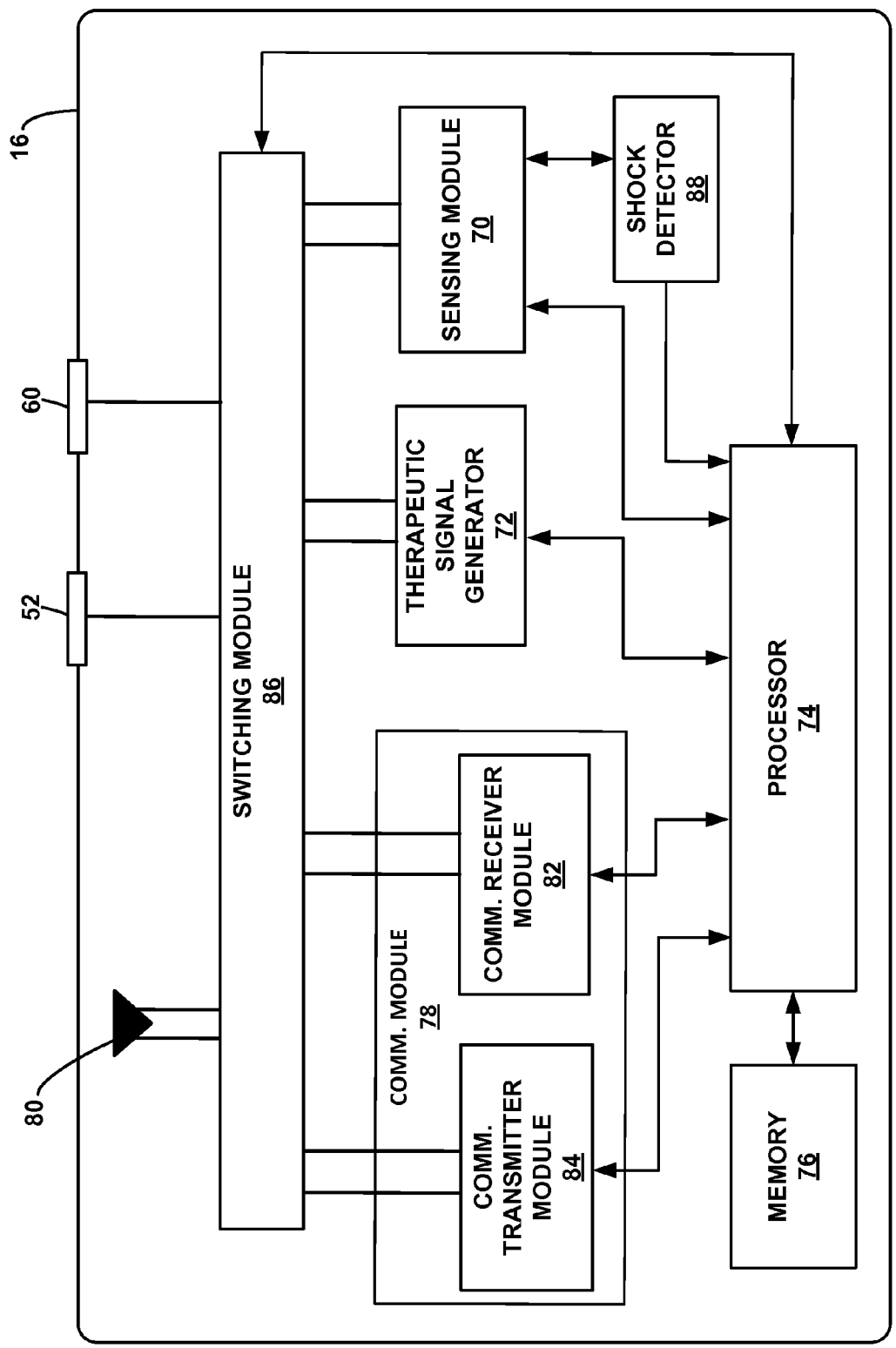
FIG. 4 is a functional block diagram illustrating an example configuration of the leadless pacing device of FIG. 1.

FIG. 4 is a functional block diagram illustrating an example configuration of LPD 16 of FIG. 1. In the illustrated example, LPD 16 includes a sensing module 70, therapeutic signal generator 72, processor 74, and memory 76. Memory 76 includes computer-readable instructions that, when executed by processor 74, cause LPD 16 and processor 74 to perform various functions attributed to LPD 16 and/or processor 74 herein (e.g., detecting arrhythmias, communicating with ICD 30, delivering anti-tachycardia pacing and post-shock pacing, and selectively coupling electrodes 52, 60 and/or antenna 80 to communication receiver module 82 and/or communication transmitter module 84). Memory 76 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 74 may include any one or more of a microprocessor, a controller, a digital signal processor (DSP), an application specific integrated circuit (ASIC), a field-programmable gate array (FPGA), or equivalent discrete or analog logic circuitry. In some examples, processor 74 may include multiple components, such as any combination of one or more microprocessors, one or more controllers, one or more DSPs, one or more ASICs, or one or more FPGAs, as well as other discrete or integrated logic circuitry. The functions attributed to processor 74 herein may be embodied as software, firmware, hardware or any combination thereof.

Processor 74 controls therapeutic signal generator 72 to deliver stimulation therapy, e.g., cardiac pacing pulses, to heart 12 via electrodes 52 and 60. For example, therapeutic signal generator 72 may deliver ATP or post-shock pacing pulses to a portion of cardiac muscle within heart 12 via electrodes 52 and 60 as controlled by processor 74. Processor 74 may control therapeutic signal generator 72 to deliver the stimulation according to a therapy parameters, which may be stored in memory 76. Although in the illustrated example LPD 16 includes two electrodes, e.g., electrodes 52 and 60, LPD 16 may utilize three or more electrodes in other examples. LPD 16 may use any combination of electrodes to deliver therapy and/or detect electrical signals from patient 14.

Electrical sensing module 70 may monitor signals from electrodes 52 and 60 in order to monitor electrical activity of heart 12. Sensing may be done to determine heart rates or heart rate variability, or to detect arrhythmias (e.g., bradyarrhythmia or tachyarrhythmias), as examples. Sensing module 70 may include one or more detection channels configured to detect cardiac events, such as P- or R-waves, and provide indications of the occurrences of such events to processor 74, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

As illustrated in FIG. 4, LPD 16 also includes a communication module 78. Communication module 78 may include hardware, firmware, software or any combination thereof for communicating with another device, such as programmer 20 or ICD 30 (FIG. 1), according to the techniques described herein. In the illustrated example, communication module 78 includes a communication receiver module 82 for receiving and demodulating signals from another device, and a communication transmitter module 84 for modulating and transmitting signals to another device.

Communication receiver module 82 is configured to receive RF telemetry signals within a predetermined frequency band for RF telemetry communication via antenna 80. Antenna 80 comprises any one or more antenna elements configured to wirelessly receive and emit RF signals. In some examples, antenna 80 may comprise a plurality of antennas or antenna elements, selectable via switches, to provide antenna or signal diversity, which may improve the quality or reliability of RF telemetry communication. Communication receiver module 82 may include circuitry configured to receive and demodulate alternating signals within the predetermined frequency band for RF telemetry communication. The modulation may be, as examples, amplitude modulation (AM), frequency modulation (FM), or digital modulation (DM), such as frequency-shift keying (FSK) or phase-shift keying (PSK). One example of an FSK receiver configured to receive RF signals on an antenna is described in U.S. Pat. No. 8,798,205, entitled "Telemetry Polling Circuit with Noise Discrimination and Selectable Tuning," which issued on Aug. 5, 2014, to Ecker et al., the entire content of which is incorporated herein by reference. The data modulated on RF telemetry signal may be instructions from programmer 20, for example.

Communication receiver module 82 is also configured to receive TCC signals within the predetermined frequency band for RF telemetry communication via electrodes 52 and 60. The TCC signals may be alternating signals within the predetermined frequency band for RF telemetry communication, which may be modulated using, as examples, AM, FM, or DM, such as FSK or PSK. The TCC signals may be received from any other implanted or external device, such as ICD 30. The data modulated on TCC signals may include "wake up" commands, or commands to deliver ATP or post-shock pacing, as examples.

Communication transmitter module 84 is configured to generate an RF telemetry signal within the predetermined frequency band for RF telemetry communication, for emission via antenna 80. Communication transmitter module 84 may include an oscillator and/or other circuitry configured to generate a carrier signal at the desired frequency. Communication transmitter module 84 further includes circuitry configured to modulate data, e.g., stored physiological and/or therapy delivery data, on the carrier signal. The modulation may be, as examples, AM, FM, or DM, such as FSK or PSK.

Communication transmitter module 84 may also be configured transmit TCC signals within the predetermined frequency band for RF telemetry communication via electrodes 52 and 60. The TCC signals may include a carrier signal generated by the oscillator and/or other circuitry at the desired frequency, modulated using, as examples, AM, FM, or DM, such as FSK or PSK. The TCC signals may be received from any other implanted or external device, such as ICD 30. The data modulated on TCC signals may include, as examples, indications that a cardiac depolarization or tachyarrhythmia was detected, or that cardiac pacing was delivered.

The predetermined frequency band for RF telemetry communication, which communication receiver module 82 and/or communication transmitter module 84 may use for both RF telemetry communication and TCC, may be greater than or equal to approximately 100 kHz. In some examples, the predetermined frequency band for RF telemetry communication may be within a range from approximately 150 kHz to approximately 200 kHz. A biphasic current waveform, such as a TCC signal emitted or received by electrodes 52 and 60, at a frequency of at least 100 kHz may be less likely to stimulate nearby tissue, e.g., muscles or nerves, or cause pain than lower frequency waveforms. In some examples, the modulation is FM toggling between approximately 150 kHz and approximately 200 kHz. In some examples, although communication transmitter module 84 transmits both RF telemetry and TCC signals within the same frequency band, e.g., within a range from approximately 150 kHz to approximately 200 kHz, the modulation techniques for the two signals may be different. For example, communication transmitter module 84 may transmit RF telemetry signals at 175 kHz using PSK modulation at 87.5 kilo-bytes per second (kbps), and transmit TCC signals at 150 kHz/200 kHz using FSK modulation at 12.5 kbps.

In the example illustrated in FIG. 4, LPD 16 further includes a switching module 86 configured to selectively couple receiver module 82 and transmitter module 84 to either antenna 80 for RF telemetry or electrodes 52 and 60 for TCC. Additionally, in the example illustrated in FIG. 4, switching module 86 is configured to selectively couple electrodes 52 and 60 to one of receiver module 82, transmitter module 84, sensing module 70, or therapeutic signal generator 72, depending on whether LPD 16 is receiving TCC signals, sensing electrical signals of the patient, or delivering therapeutic stimulation to the patient. Switching module 86 may include any one or more devices, e.g., transistors, configured for switching, which may be arranged in an array or matrix, for example. Additionally, switching module 86 may include circuitry to buffer or amplify the signals generated on electrodes 52 and 60 prior to connection to communication receiver module 82.

Processor 74 receives the data modulated on the RF telemetry signals and TCC signals received by communication receiver module 82. For example, a TCC signal emitted by ICD 30 may include a command to deliver ATP or post-shock pacing, and processor 74 may be configured to control therapeutic signal generator 72 to deliver the at least one of ATP or post-shock pacing via electrodes 52 and 60 in response to the TCC signal. Processor 74 may also provide data to transmitter module 84 to be modulated onto a carrier signal and emitted via either antenna 80 as RF telemetry signals or via electrodes 52 and 60 as TCC signals.

Furthermore, as illustrated in FIG. 4, processor 74 may be configured to control switching module 86. For example, processor 74 may control switching module 86 to selectively couple receiver module 82 to either antenna 80 or electrodes 52 and 60. Processor 74 may also control switching module 86 to selectively couple transmitter module 84 to either antenna 80 or electrodes 52 and 60. Additionally, processor 74 may control switching module 86 to selectively control the coupling of electrodes 52 and 60 to either sensing module 70, therapeutic signal generator 72, transmitter module 82, or receiver module 84.

In some examples, processor 74 may generally control switching module 86 to couple antenna 80 to communication receiver module 82 and communication transmitter module 84 for receipt and transmission of RF telemetry signals. However, in response to processor 74 determining that a TCC signal should be delivered to another device, such as ICD 30, another LPD, or any other IMD, processor 74 may control switching module 86 to decouple transmitter module 84 from antenna 80 and couple the transmitter module to electrodes 52 and 60. Similarly, processor 74 may control switching module 86 to decouple receiver module 82 from antenna 80 and couple the receiver module to electrodes 52 and 60 to receive a TCC signal.

In some examples, processor 74 periodically controls switching module 86 to decouple receiver module 82 from antenna 80 and couple the receiver module to electrodes 52 and 60 to receive a TCC signal. As an example, every one or more seconds processor 74 may control switching module 86 to couple receiver module 82 to electrodes 52 and 60 for a period of time, such as approximately 250 milliseconds to look for a TCC signal. In some examples, such as when polling for a TCC signal, the frequency of coupling of receiver module 82 to electrodes 52 and 60 may be greater, such as approximately every 250 milliseconds, and the period of that the electrodes remain coupled to the receiver module may be within a range from approximately 0.1 millisecond to 1 millisecond. A technique for polling for TCC signals that may be efficient in terms or current drawn and/or power consumed, and may be implanted by processor 74, switching module 86, and receiver module 82, is to poll for a TCC signal immediately after polling for an RF telemetry signal. Such a technique may also reduce the likelihood that currents induced in or on an IMD by an RF telemetry signal would be incorrectly detected as a TCC signal.

Once a TCC signal has been detected, processor 74 may control switching module 86 to couple receiver module 82 to electrodes 52 and 60 for a longer period of time, such as within a range from approximately 100 milliseconds to approximately 1000 milliseconds. In some examples, the TCC signal may include a "wake up" signal, which may be approximately 250 milliseconds in length, and a message that may last a few milliseconds. In some examples, a device, e.g., ICD 30, may transmit a message to LPD 16 via TCC multiple times to increase the likelihood that the LPD receives the message. For example, the device may transmit the message multiple times during a cardiac cycle. The orientation of LDP 16 relative to the device, e.g., ICD 30, may change during the cardiac cycle, and transmitting the message multiple times during the cardiac cycle may increase the likelihood that LPD 16 is oriented relative to the device such that it is able to receive the TCC signal. In some examples, a device, such as ICD 30, transmitting a TCC signal to LPD 16 may send three to four copies of a "wake up" signal and a message during an approximately 1 second period.

In some examples, processor 74 controls switching module 86 to decouple receiver module 82 from antenna 80 and couple the receiver module to electrodes 52 and 60 to receive a TCC signal in response to detecting an event or condition which suggests that receipt of a TCC signal is likely. For example, ICD 30 may send a TCC signal instructing LPD 16 to deliver ATP in response to detecting a tachyarrhythmia. To detect such a TCC signal, processor 74 may control switching module 86 to decouple receiver module 82 from antenna 80 and couple the transmitter module to electrodes 52 and 60 to receive a TCC signal in response to detecting a heart rate (or one or more cardiac cycle lengths associated with a heart rate) over a threshold value. The threshold value may correspond to heart rates within a range from approximately 160 beats-per-minute to approximately 200 beats-per-minute, as an example. As another example, ICD 30 may send a TCC signal instructing LPD 16 to deliver post-shock pacing in response to delivering a shock that terminates a tachyarrhythmia. To detect such a TCC signal, processor 74 may control switching module 86 to decouple receiver module 82 from antenna 80 and couple the receiver module to electrodes 52 and 60 to receive a TCC signal in response to detecting a shock delivered by extravascular ICD system 15.

As illustrated in FIG. 4, LPD 16 may include a shock detector 88 used to detect anti-tachyarrhythmia shocks delivered by extravascular ICD system 15 or another device or system. For example, processor 74 may enable shock detector 88 in response to detecting a tachyarrhythmia, e.g., in response to detecting a heart rate (or one or more cardiac cycle lengths associated with a heart rate) over the threshold value. Processor 74 may also disable shock detector 88 after a predetermined time period has elapsed or a shock is otherwise not anticipated. When shock detector 88 is enabled, shock detector 88 may analyze a signal sensed by sensing module 70 to determine whether a waveform representative of an artificial anti-tachyarrhythmia shocks shock pulse is present in the signal. In response to detecting such a waveform, shock detector 88 provides an indication of detection of a shock to processor 74.

Although in the example illustrated in FIG. 4 both receiver module 82 and transmitter module 84 may be selectively coupled to electrodes 52 and 60 for TCC, in other examples only one of receiver module 82 or transmitter module 84 is coupleable to electrodes 52 and 60 for TCC. In such examples, the one of receiver module 82 or transmitter module 84 may be coupled to switching module 86, while the other need not be. The other of receiver module 82 or transmitter module 84 may be coupled to antenna 80 for RF telemetry, but not through switching module 86.

In some examples, receiver module 82 may be selectively coupled to antenna 80 or electrodes 52 and 60 by switching module 86 for receipt of RF telemetry or TCC signals, while transmitter module 84 remains fixedly coupled to antenna 80 for RF telemetry communication. In such examples, receiver module 82 and transmitter module 84 are both configured for RF telemetry communication, e.g., to make LPD 16 capable bi-directional RF telemetry communication with programmer 20. However, in such examples, receiver module 82 is configured to receive TCC signals, but transmitter module 84 is not configured to transmit TCC signals, e.g., to make LPD 16 capable of uni-directional TCC as a receiver. Such a configuration of communication module 78 may be used if, for example, LPD 16 is configured as a slave to another IMD, e.g., ICD 30 as described herein, in a master-slave relationship.

In other examples, communication module 78 may be oppositely configured, with transmitter module 84 (and not receiver module 82) coupleable to electrodes 52 and 60 for TCC. In some examples, LPD 16 may act as a master in a master-slave relationship, e.g., to ICD 30 or another LPD. In some examples, LPD 16 may detect tachyarrhythmia and command ICD 30 to deliver shocks, or may detect a depolarization in one chamber of heart 12 and provide an indication of the depolarization to an LPD in another chamber for delivery of pacing to the other chamber.

In this manner, LPD 16 is an example of an IMD configured for implantation in a patient comprising an antenna, a plurality of electrodes, and a communication module. The communication module comprises at least one of: a communication receiver module configured to receive and demodulate signals within a predetermined frequency band for RF telemetry communication, wherein the communication receiver module is configured to receive from the antenna and demodulate a first RF telemetry signal emitted by an external device outside of the patient, and receive from the plurality of electrodes and demodulate a first TCC signal emitted by another implantable medical device implanted within the patient, wherein the first RF telemetry signal and the first TCC signal are within the predetermined band for RF telemetry communication; or a communication transmitter module configured to modulate and transmit signals within the predetermined frequency band for RF telemetry communication, wherein the communication transmitter module is configured to modulate and transmit a second RF telemetry signal to the external device via the antenna, and modulate and transmit a second TCC signal to the other implantable medical device via the plurality of electrodes, wherein the second RF telemetry signal and the second TCC signal are within the predetermined band for RF telemetry communication.

Figure 5:
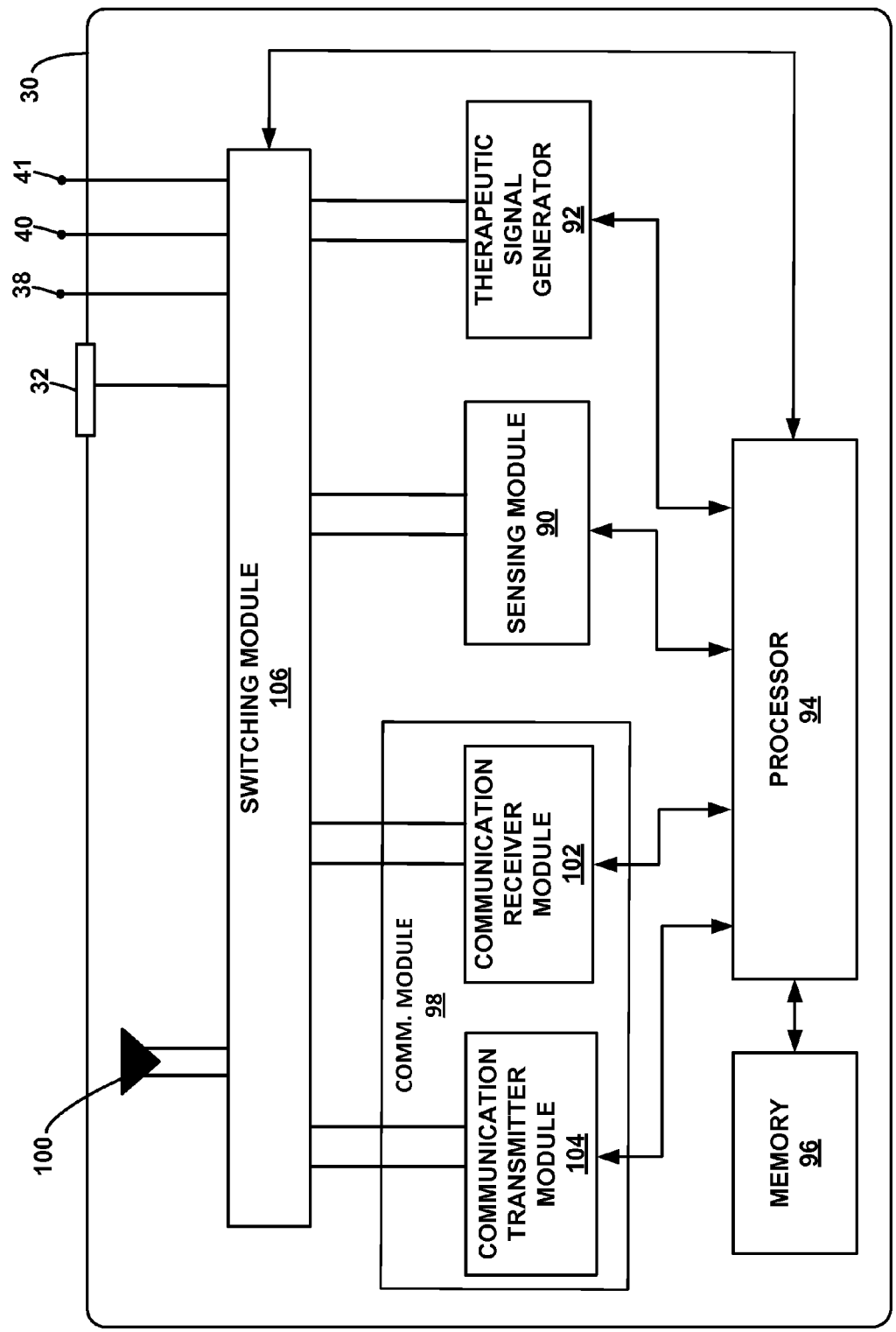
FIG. 5 is a functional block diagram illustrating an example configuration of the extravascular implantable cardioverter defibrillator of FIG. 1.

FIG. 5 is a functional block diagram illustrating an example configuration of ICD 30 of FIG. 1. In the illustrated example, ICD 30 includes a sensing module 90, therapeutic signal generator 92, processor 94, and memory 96. Memory 96 includes computer-readable instructions that, when executed by processor 94, cause ICD 30 and processor 94 to perform various functions attributed to ICD 30 and processor 94 herein (e.g., detection of tachyarrhythmias, communication with LPD 16, and/or delivery of anti-tachyarrhythmia shock therapy). Memory 96 may include any volatile, non-volatile, magnetic, optical, or electrical media, such as a RAM, ROM, NVRAM, EEPROM, flash memory, or any other digital or analog media.

Processor 94 may include any one or more of a microprocessor, a controller, a DSP, an ASIC, a FPGA, or equivalent discrete or analog logic circuitry. In some examples, processor 94 may include multiple components, such as any combination of one or more microprocessors, one or more controllers, one or more DSPs, one or more ASICs, or one or more FPGAs, as well as other discrete or integrated logic circuitry. The functions attributed to processor 94 herein may be embodied as software, firmware, hardware or any combination thereof.

Processor 94 controls therapeutic signal generator 92 to deliver therapeutic signals, e.g., anti-tachyarrhythmia shocks, such as defibrillation shocks and/or cardioversion shocks, to heart 12 according to a therapy parameters, which may be stored in memory 96. For example, processor 94 may control therapeutic signal generator 92 to deliver shock pulses with the amplitudes, pulse widths, frequency, electrode polarities, and progression specified by the therapy parameters, e.g., via housing electrode 32 and defibrillation electrode 38. Therapeutic signal generator 92 may include circuitry and/or capacitors required to deliver an anti-tachyarrhythmia shock. For example, therapeutic signal generator 92 may charge capacitors to prepare for delivering a shock, and may then discharge the capacitors to enable therapeutic signal generator 92 to deliver the shock to patient 14 via one or more electrodes.

Electrical sensing module 90 may be configured to monitor signals from at least one of electrodes 32, 38, 40 and 41 in order to monitor electrical activity of heart 12, impedance, or other electrical phenomenon. Sensing may be done to determine heart rates or heart rate variability, or to detect arrhythmias (e.g., tachyarrhythmia) or other electrical signals. Sensing module 90 may also use switching module 106 to select which of the available electrodes are used to sense the heart activity, depending upon which electrode combination, or electrode vector, is used in the current sensing configuration. In examples with several electrodes, processor 94 may select the electrodes that function as sense electrodes, i.e., select the sensing configuration, via switching module 106. Sensing module 90 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 94, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Processor 94 may implement interval counters, which may be reset upon sensing of R-waves and P-waves by sensing module 90. The value of the count present in the interval counters when reset by sensed R-waves and P-waves may be used by processor 94 to measure the durations of R-R intervals, P-P intervals, P-R intervals and R-P intervals, which are measurements that may be stored in memory 96. Processor 94 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 96 may be configured as a plurality of recirculating buffers, capable of holding series of measured intervals, which may be analyzed by processor 94 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 94 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREAT- MENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies, such as those methodologies that utilize timing and morphology of the electrocardiogram, may also be employed by processor 94 in other examples.

Memory 96 may be configured to store a variety of operational parameters, therapy parameters, sensed and detected data, and any other information related to the monitoring, therapy and treatment of patient 14. Memory 96 may store, for example, thresholds and parameters indicative of tachyarrhythmias and/or therapy parameter values that at least partially define delivered anti-tachyarrhythmia shocks. In some examples, memory 96 may also store communications transmitted to and/or received from LPD 16.

As illustrated in FIG. 5, ICD 30 also includes a communication module 98, switching module 106 and antenna 100. Communication module 98 may include hardware, firmware, software or any combination thereof for communicating with another device, such as programmer 20 or LPD 16 (FIG. 1), according to the techniques described herein. In the illustrated example, communication module 98 includes a communication receiver module 102 for receiving RF telemetry and TCC signals from another device, and a communication transmitter module 104 for transmitting RF telemetry and TCC signals to another device.

Antenna 100, communication receiver module 102, communication transmitter module 104, and switching module 106 may be configured substantially as described above with respect to antenna 80, communication receiver module 82, communication transmitter module 84, and switching module 86 of LPD 16, respectively, illustrated in FIG. 4. For example, switching module 106 may be configured to selectively couple any two or more of electrodes 32, 38, 40 and 41, e.g., electrodes 32 and 38, to communication receiver module 102 for receipt of a TCC signal, e.g., from LPD 16, or transmission of a TCC signal, e.g., to LPD 16. Processor 94 may be configured to control switching module 106, e.g., as described above with respect to processor 74 of LPD 16 in FIG. 4, as well as provide data to transmitter module 104 and receive data from receiver module 102.

Although in the example illustrated in FIG. 5 both receiver module 102 and transmitter module 104 may be selectively coupled to the electrodes for TCC, in other examples only one of receiver module 102 or transmitter module 104 is coupleable to the electrodes for TCC. In such examples, the one of receiver module 102 or transmitter module 104 may be coupled to switching module 106, while the other need not be. The other of receiver module 102 or transmitter module 104 may be coupled to antenna 100 for RF telemetry, but not through switching module 106.

In some examples, transmitter module 104 may be selectively coupled to antenna 100 or electrodes 32, 38, 40, and 41 by switching module 106 for transmission of RF telemetry or TCC signals, while receiver module 102 remains fixedly coupled to antenna 100 for RF telemetry communication. In such examples, receiver module 102 and transmitter module 104 are both configured for RF telemetry communication, e.g., to make ICD 30 capable of bi-directional RF telemetry communication with programmer 20. However, in such examples, transmitter module 104 is configured to transmit TCC signals, but receiver module 102 is not configured to receive TCC signals, e.g., to make ICD 30 capable of uni-directional TCC as a transmitter. Such a configuration of communication module 98 may be used if, for example, ICD 30 is configured as a master to another IMD, e.g., LPD 16 as described herein, in a master-slave relationship.

In other examples, communication module 98 may be oppositely configured, with receiver module 102 (and not transmitter module 104) coupleable to the electrodes for TCC. In some examples, ICD 30 may act as a slave in a master-slave relationship, e.g., to LPD 16. In some examples, LPD 16 may detect tachyarrhythmia and command ICD 30 to deliver shocks via a TCC signal.

Furthermore, although described herein in the context of a cardiac system 10 in which at least one of receiver module 102 and transmitter module 104 is capable of being selectively coupled to either antenna 100 for RF telemetry or electrodes 32, 38, 40, and 41 for TCC, in other examples ICD 30 may instead include respective modules/circuitry for RF telemetry and TCC. Because ICD 30 is implanted subcutaneously outside of a ribcage of patient 14, housing 31 may be able to have a volume sufficient, e.g., greater than LPD 16, to allow specialized circuitry for transmitting and/or receiving TCC signals, separate from its RF telemetry circuitry.

For example, ICD 30 may include a separate TCC signal generator, e.g., current driver, coupleable to two or more of electrodes 32, 38, 40, and 41 to transmit TCC signals. To communicate with LPD 16 including receiver module 82 described herein, the TCC signal generator may generate an alternating signal, e.g., pulse train, at a frequency within the predetermined frequency range for RF telemetry communication. The TCC signal generator may be configured to modulate data on the TCC signal using, as example, AM, FM, or DM, such as FSK modulation or PSK modulation. In some examples, switching module 106 may be configured to selectively couple the TCC signal generator to any two or more of electrodes 32, 38, 40 and 41, e.g., can electrode 32 and defibrillation electrode 38, for transmission of a TCC signal.

The TCC signal generator may facilitate "one-way" TCC from ICD 30 to LPD 16, to provide commands for ATP and post-shock pacing. In some examples, ICD 30 may additionally or alternatively include a separate TCC receiver module to facilitate "two-way" TCC between ICD 30 and LPD 16. The separate TCC receiver module may have more sensitivity than an RF telemetry receiver module, e.g., to compensate for lower signal-to-noise ratio TCC signals from LPD 16. LPD 16 may generate relatively lower signal-to-noise ratio TCC signals by generating relatively smaller amplitude signals. LPD 16 may generate relatively smaller amplitude TCC signals due to its smaller power source, and/or to avoid stimulation of adjacent tissue because electrodes 50 and 62 of LPD 16 may have a relatively short separation distance and/or small surface area and, accordingly, higher current density for a given TCC signal amplitude.

Additionally, although described primarily with respect to examples in which TCC from ICD 30 to LPD 16 is to command LPD 16 to deliver cardiac pacing, the TCC may additionally or alternatively be for other purposes. For example, ICD 30 and/or LPD 16 may transmit and/or receive TCC signals to test the operation of TCC. In one example, ICD 30 may send a TCC message to LPD 16 to shorten a pacing interval for one or more beats, and detect implementation of the shortened pacing interval by detecting pacing pulses or resulting depolarizations with sensing module 90 via one or more of electrodes 32, 38, 40, or 41. Based on detecting the shortened pacing interval, ICD 30 may confirm the availability of TCC with LPD 16.

In some examples, transmitter module 104, or a separate TCC signal generator, is configured to transmit a message via TCC signals, e.g., to LPD 16, multiple times to increase the likelihood that the LPD receives the message. For example, the transmitter module 104 or a separate TCC signal generator may transmit the message multiple times during a cardiac cycle. The orientation of LDP 16 relative to the electrodes of ICD 30, may change during the cardiac cycle, and transmitting the message multiple times during the cardiac cycle may increase the likelihood that LPD 16 is oriented relative to the transmitting electrodes such that it is able to receive the TCC signal. Although described herein in the context of examples in which ICD 30 transmits a messages multiple times, ICD 30 sends a test message to LPD 16 to shorten a pacing interval, LPD 16 shortens a pacing interval in response to the test message, and ICD 30 detects the shortened pacing interval to confirm availability of TCC, the roles of ICD 30 and LPD 16 may be reversed, or performed by any one or more IMDs that communicate via TCC.

In this manner, ICD 30 is an example of an IMD configured for implantation in a patient comprising an antenna, a plurality of electrodes, and a communication module. The communication module comprises at least one of: a communication receiver module configured to receive and demodulate signals within a predetermined frequency band for RF telemetry communication, wherein the communication receiver module is configured to receive from the antenna and demodulate a first RF telemetry signal emitted by an external device outside of the patient, and receive from the plurality of electrodes and demodulate a first TCC signal emitted by another implantable medical device implanted within the patient, wherein the first RF telemetry signal and the first TCC signal are within the predetermined band for RF telemetry communication; or a communication transmitter module configured to modulate and transmit signals within the predetermined frequency band for RF telemetry communication, wherein the communication transmitter module is configured to modulate and transmit a second RF telemetry signal to the external device via the antenna, and modulate and transmit a second TCC signal to the other implantable medical device via the plurality of electrodes, wherein the second RF telemetry signal and the second TCC signal are within the predetermined band for RF telemetry communication.

Figure 6:
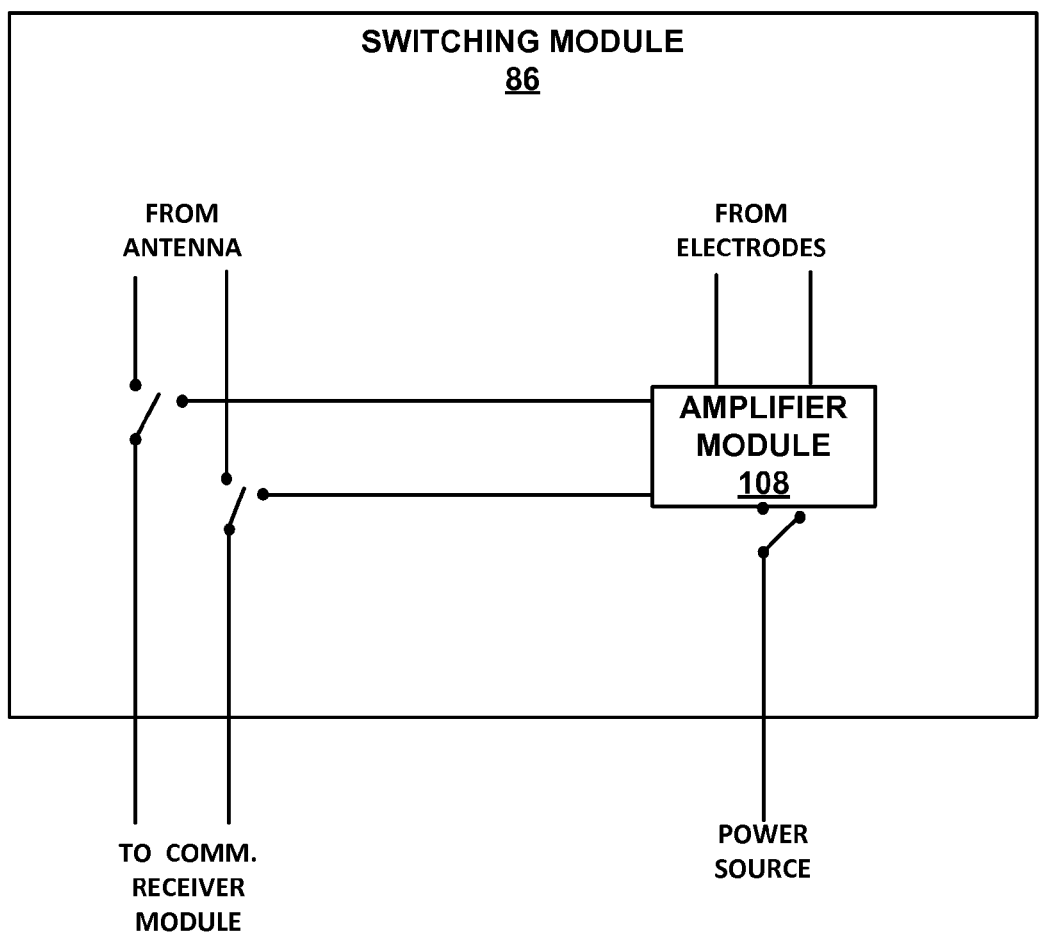
FIG. 6 is a functional block diagram further illustrating an example switching module of an implantable medical device.

FIG. 6 is a functional block diagram further illustrating an example switching module of an IMD. Although FIG. 6 illustrates switching module 86 of LPD 16, switching module 106 of ICD 30 may be similarly configured. As illustrated by FIG. 6, an IMD, e.g. LPD 16, may include an amplifier module 108, which may be included as part of a switching module, e.g., switching module 86.

Amplifier module 108 amplifies the TCC signal prior to receipt by communication receiver module 82, but does not amplify the RF telemetry signal prior to receipt by the communication module. In the illustrated example, amplifier module 108 is included in an electrical path from electrodes 52 and 60 to communication receiver module 82, but is not included in the electrical path from antenna 80 to communication receiver module 82. Additionally or alternatively, amplifier module 108 may be turned on or otherwise activated, e.g., by processor 74, when processor 74 is expecting to receive a TCC signal or polling for a TCC signal, and may otherwise be turned off or otherwise inactive. In the example illustrated by FIG. 6, amplifier module 108 is selectively coupled to a power source when is expecting to receive a TCC signal or polling for a TCC signal, and is otherwise decoupled from the power source. Amplifier module 108 may be, in some examples, a pre-amplifier, which may amplify the TCC signal three or four times its received amplitude, for example.

Figure 7:
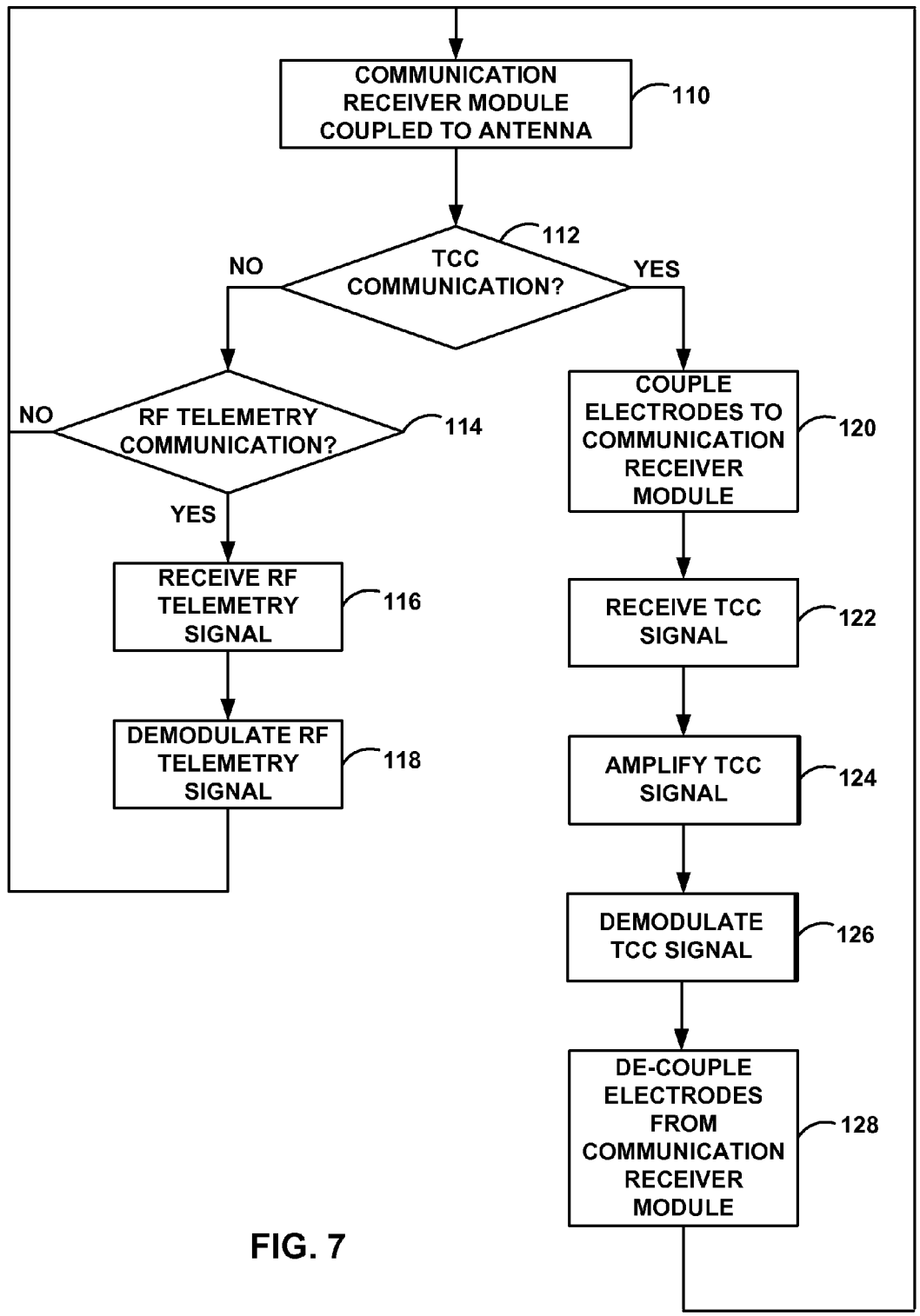
FIG. 7 is a flow diagram illustrating an example method for receiving and demodulating both radio-frequency (RF) telemetry signals and tissue conductance communication (TCC) signals with a common communication receiver module of an implantable medical device.

FIG. 7 is a flow diagram illustrating an example method for receiving and demodulating both RF telemetry signals and TCC signals with a common communication receiver module of an IMD. The example method of FIG. 7 will be described with respect to LPD 16, but may be implemented by ICD 30, or any other IMD.

According to the example of FIG. 7, communication receiver module 82 is coupled to antenna 80, e.g., selectively coupled via switching module 86 under control of processor 74 (110). Processor 74 may determine whether a TCC communication is expected, or otherwise determine whether it is time to check for a TCC signal (112). For example, processor 74 may periodically poll for a TCC signal, or poll for a TCC signal in response to detecting an event or a condition, such as a heart rate greater than a threshold or a therapeutic shock, as described herein.

When processor 74 does not anticipate receiving a TCC signal (NO of 112), communication receiver module 82 remains coupled to antenna 80, and may determine whether to engage in RF telemetry communication e.g., has received an RF telemetry communication via the antenna, or data for RF telemetry transmission from processor 74 (114). If engaged in RF telemetry communication (YES of 114), communication receiver module 82 may receive an RF telemetry signal from antenna 80 (116), and demodulate the RF telemetry signal (118).

When processor 74 anticipates receiving a TCC signal, or periodically checks for a TCC signal (YES of 112), processor 74 may control switching module 86 to selectively couple electrodes 50 and 62 to communication receiver module 82 (120). Processor 74 may also control switching module 86 to decouple antenna 80 from communication receiver module 82, and to decouple sensing module 70 and therapeutic signal generator 72 from electrodes 50 and 62. Electrodes 50 and 62 may then receive a TCC signal (122), amplifier module 108 may amplify the TCC signal, e.g., as described above with respect to FIG. 6 (124), and communication receiver module 82 may demodulate the TCC signal (126).

After receipt of the TCC signal, processor 74 may control switching module 86 to decouple electrodes 52 and 60 from communication receiver module 82 (128). Processor 74 may also control switching module 86 to couple antenna 80 to communication receiver module 82, and to couple electrodes 50 and 62 to sensing module 70 and/or signal generator 72. Processor 74 may receive the data included in the TCC signal, and act on the data, e.g., control therapeutic signal generator 72 to generate ATP or post-shock pacing for delivery via electrodes 50 and 62.

Figure 8:
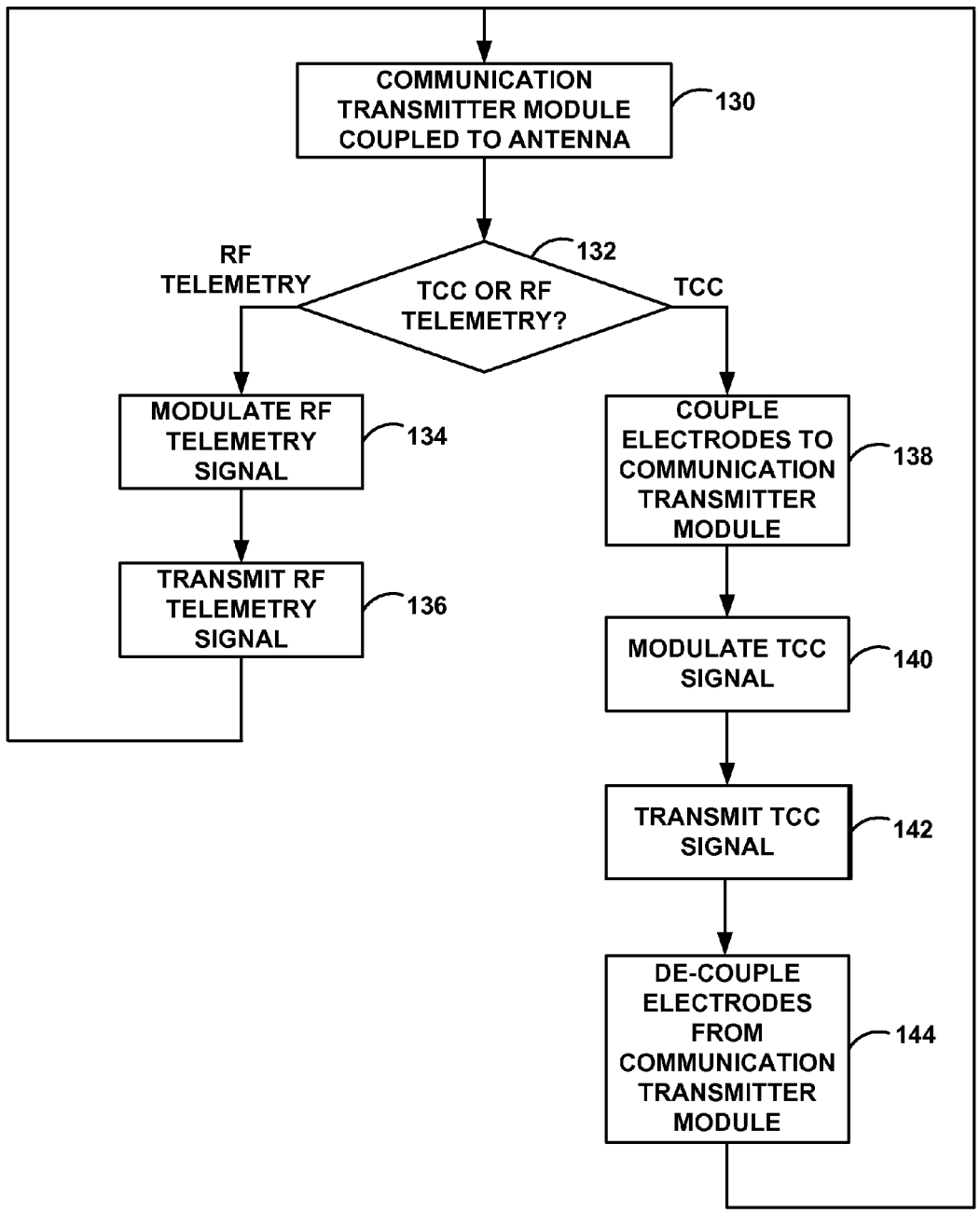
FIG. 8 is a flow diagram illustrating an example method for modulating and transmitting both RF telemetry signals and TCC signals with a common communication transmitter module of an implantable medical device.

FIG. 8 is a flow diagram illustrating an example method for modulating and transmitting both RF telemetry signals and TCC signals with a common communication transmitter module of an implantable medical device. The example method of FIG. 8 will be described with respect to LPD 16, but may be implemented by ICD 30, or any other IMD.

According to the example of FIG. 8, communication transmitter module 84 is coupled to antenna 80, e.g., selectively coupled via switching module 86 under control of processor 74 (130). Processor 74 may determine whether to transmit a TCC signal, e.g., to ICD 30, or RF telemetry signal, e.g., to programmer 20 (132). When processor 74 determines to transmit an RF telemetry signal (RF TELEMETRY of 132), communication transmitter module 84 remains coupled to antenna 80. Communication transmitter module 84 modulates an RF telemetry signal (134), and transmits the RF telemetry signal via antenna 80 (136).

When processor 74 determines to transmit a TCC signal (TCC of 132), processor 74 may control switching module 86 to selectively couple electrodes 50 and 62 to communication transmitter module 84 (138). Processor 74 may also control switching module 86 to decouple antenna 80 from communication transmitter module 84, and to decouple sensing module 70 and therapeutic signal generator 72 from electrodes 50 and 62. Transmitter module 84 may then modulate the TCC signal (140), and transmit the TCC signal via electrodes 50 and 62 (142). After transmission of the TCC signal, processor 74 may control switching module 86 to decouple electrodes 52 and 60 from communication transmitter module 84 (142). Processor 74 may also control switching module 86 to couple antenna 80 to communication transmitter module 84, and to couple electrodes 50 and 62 to sensing module 70 and/or therapeutic signal generator 72.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to ICD 30, LPD 16, programmer 20, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between ICD 30, LPD 16 and/or programmer 20. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described for facilitating TCC between IMDs. Any combination of the described operations or functions is contemplated. These and other examples are within the scope of the following claims.

What is claimed is:

1. An implantable medical device configured for implantation in a patient comprising:
    an antenna;
    a sensing module configured to receive a cardiac electrogram of the patient via a plurality of electrodes;
    a communication receiver module configured to receive and demodulate signals within a predetermined frequency band for radio-frequency (RF) telemetry communication, wherein the communication receiver module is configured to receive from the antenna and demodulate a first RF telemetry signal emitted by an external device outside of the patient, and receive from the plurality of electrodes and demodulate a first tissue conduction communication (TCC) signal emitted by another implantable medical device implanted within the patient, wherein the first RF telemetry signal and the first TCC signal are within the predetermined band for RF telemetry communication;
    a switching module comprising one or more switches, wherein the switching module is configured to selectively couple the plurality of electrodes to either the sensing module or the communication receiver module; and
    a processor configured to:
        determine a heart rate of the patient based on depolarizations sensed by the sensing module in the cardiac electrogram;
        determine that the heart rate is greater than a threshold value; and
        change the switching module from a first configuration in which the antenna is coupled to the communication receiver module and the plurality of electrodes are decoupled from the communication receiver module to a second configuration in which the antenna is decoupled from the communication receiver module and the plurality of electrodes are coupled to the communication receiver module in response to the determination that the heart rate is greater than the threshold value.

2. The implantable medical device of claim 1, further comprising a communication transmitter module, wherein the switching module is configured to selectively couple either the antenna or the plurality of electrodes to at least one of the communication receiver module or the communication transmitter module,
wherein the communication transmitter module is configured to modulate and transmit signals within the predetermined frequency band for RF telemetry communication, wherein the communication transmitter module is configured to modulate and transmit a second RF telemetry signal to the external device via the antenna, and modulate and transmit a second TCC signal to the other implantable medical device via the plurality of electrodes, wherein the second RF telemetry signal and the second TCC signal are within the predetermined band for RF telemetry communication.

3. The implantable medical device of claim 2, wherein the implantable medical device comprises a leadless pacing device comprising:
a therapeutic signal generator configured to deliver cardiac pacing pulses to a heart of the patient via the plurality of electrodes; and
a housing configured for implantation within the heart of the patient, wherein the housing encloses the antenna, the communication receiver module, the communication transmitter module, the switching module, the sensing module, and the therapeutic signal generator, and wherein the housing comprises or is connected to at least one electrode of the plurality of electrodes, and
wherein the switching module is configured to selectively couple the plurality of electrodes to at least one of:
the sensing module;
the therapeutic signal generator;
the communication receiver module; or
the communication transmitter module.

4. The implantable medical device of claim 3, wherein the housing encloses the processor, wherein the processor is further configured to receive the demodulated first RF telemetry signal and the demodulated first TCC signal, wherein the first TCC signal is emitted by an extravascular implantable cardioverter defibrillator implanted within the patient and includes a command to deliver at least one of anti-tachycardia pacing (ATP) or post-shock pacing, and wherein the processor is further configured to control the therapeutic signal generator to deliver the at least one of ATP or post-shock pacing via the plurality of electrodes in response to the TCC signal.

5. The implantable medical device of claim 4, wherein the processor is further configured to:
detect a shock delivered by the extravascular implantable cardioverter defibrillator based on cardiac electrogram received by the sensing module; and
change the switching module from the first configuration to the second configuration in response to the detection of the shock.

6. The implantable medical device of claim 1, wherein the processor is further configured to receive the demodulated first RF telemetry signal and the demodulated first TCC signal, wherein the processor is configured to periodically:
change the switching module from the first configuration to the second configuration;
check for the first TCC signal with the switching module in the second configuration; and
return the switching module to the first configuration after checking for the TCC signal.

7. The implantable medical device of claim 1, further comprising a communication transmitter module,
wherein the communication transmitter module is configured to modulate and transmit signals within the predetermined frequency band for RF telemetry communication, wherein the communication transmitter module is configured to modulate and transmit a second RF telemetry signal to the external device via the antenna, and modulate and transmit a second TCC signal to the other implantable medical device via the plurality of electrodes, wherein the second RF telemetry signal and the second TCC signal are within the predetermined band for RF telemetry communication,
wherein the communication transmitter module is further configured to transmit the second TCC signal to a leadless pacing device implanted within the patient, and
wherein the second TCC signal includes a command to deliver at least one of anti-tachycardia pacing (ATP) or post-shock pacing.

8. The implantable medical device of claim 1, wherein the implantable medical device comprises an extravascular implantable cardioverter defibrillator comprising:
a therapeutic signal generator configured to deliver therapeutic shocks to a heart of the patient via the plurality of electrodes; and
a communication transmitter module,
wherein the switching module is configured to selectively couple the plurality of electrodes to at least one of:
the sensing module;
the therapeutic signal generator;
the communication receiver module; or
the communication transmitter module,
wherein the communication transmitter module is configured to modulate and transmit signals within the predetermined frequency band for RF telemetry communication, wherein the communication transmitter module is configured to modulate and transmit a second RF telemetry signal to the external device via the antenna, and modulate and transmit a second TCC signal to the other implantable medical device via the plurality of electrodes, wherein the second RF telemetry signal and the second TCC signal are within the predetermined band for RF telemetry communication.

9. The implantable medical device of claim 1, further comprising:
a therapeutic signal generator configured to deliver a therapeutic electrical signal to the patient via at least one electrode of the plurality of electrodes; and
a communication transmitter module, wherein the switching module is configured to selectively couple the at least one electrode to either:
the therapeutic signal generator;
the communication receiver module; or
the communication transmitter module,
wherein the communication transmitter module is configured to modulate and transmit signals within the predetermined frequency band for RF telemetry communication, wherein the communication transmitter module is configured to modulate and transmit a second RF telemetry signal to the external device via the antenna, and modulate and transmit a second TCC signal to the other implantable medical device via the plurality of electrodes, wherein the second RF telemetry signal and the second TCC signal are within the predetermined band for RF telemetry communication.

10. The implantable medical device of claim 1, further comprising an amplifier that amplifies the first TCC signal prior to receipt by the communication receiver module, wherein the amplifier does not amplify the first RF telemetry signal prior to receipt by the communication receiver module.

11. The implantable medical device of claim 1, wherein the predetermined band for RF telemetry communication comprises signals within a range from approximately 150 kilohertz to approximately 200 kilohertz.

12. A method for receiving and demodulating both radio-frequency (RF) telemetry signals and tissue conduction communication (TCC) signals with a common communication receiver module of an implantable medical device, the method comprising:
  receiving, by a sensing module of the implantable medical device, a cardiac electrogram of the patient via a plurality of electrodes coupled to the implantable medical device;
  receiving, by the communication receiver module, an RF telemetry signal emitted by an external device outside of the patient via an antenna of the implantable medical device, wherein the RF telemetry signal is within a predetermined frequency band for RF telemetry communication;
  demodulating, by the communication receiver module, the RF telemetry signal;
  receiving, by the communication receiver module, a TCC signal emitted by another implantable medical device implanted within the patient via the plurality of electrodes, wherein the TCC signal is within the predetermined frequency band for RF telemetry communication;
  demodulating, by the communication receiver module, the TCC signal;
  selectively coupling, by a switching module of the implantable medical device comprising one or more switches, the plurality of electrodes to either the sensing module or the communication receiver module of the implantable medical device;
  determining, by a processor of the implantable medical device, a heart rate of the patient based on depolarizations sensed by the sensing module in the cardiac electrogram;
  determining, by the processor, that the heart rate is greater than a threshold value; and
  changing, by the processor, the switching module from a first configuration in which the antenna is coupled to the communication receiver module and the plurality of electrodes are decoupled from the communication receiver module to a second configuration in which the antenna is decoupled from the communication receiver module and the plurality of electrodes are coupled to the communication receiver module in response to the determination that the heart rate is greater than the threshold value.

13. The method of claim 12, wherein the implantable medical device comprises a leadless pacing device comprising:
  a therapeutic signal generator configured to deliver cardiac pacing pulses to a heart of the patient via the plurality of electrodes; and
  a housing configured for implantation within the heart of the patient, wherein the housing encloses the antenna, the communication receiver module, the switching module, the sensing module, and the therapeutic signal generator, and wherein the housing comprises or is connected, to the plurality of electrodes,
  the method further comprising selectively coupling, with the switching module, the plurality of electrodes to at least one of the communication receiver module, the sensing module, or the therapeutic signal generator.

14. The method of claim 13, wherein the TCC signal is emitted by an extravascular implantable cardioverter defibrillator implanted within the patient and includes a command to deliver at least one of anti-tachycardia pacing (ATP) or post-shock pacing, the method further comprising delivering the at least one of ATP or post-shock pacing via the plurality of electrodes in response to the TCC signal.

15. The method of claim 14, further comprising:
  detecting a shock delivered by the extravascular implantable cardioverter defibrillator based on cardiac electrogram received by the sensing module; and
  changing the switching module from the first configuration to the second configuration in response to the detection of the shock.

16. The method of claim 12, wherein the implantable medical device comprises a therapeutic signal generator configured to deliver a therapeutic electrical signal to the patient via the plurality of electrodes, the method further comprising selectively coupling, with the switching module, the plurality of electrodes to at least one of the communication receiver module, the sensing module, or the therapeutic signal generator.

17. The method of claim 12, further comprising amplifying, with an amplifier of the implantable medical device, the TCC signal prior to demodulating, by the communication receiver module, the TCC signal, wherein the amplifier does not amplify the RF telemetry signal prior to receipt by the communication module.

18. A method for modulating and transmitting both radio-frequency (RF) telemetry signals and tissue conduction communication (TCC) signals with a common communication transmitter module of an implantable medical device, the method comprising:
  receiving, by a sensing module of the implantable medical device, a cardiac electrogram of the patient via a plurality of electrodes;
  modulating, by the communication transmitter module, an RF telemetry signal;
  transmitting, by the communication transmitter module, the RF telemetry signal to an external device outside of the patient via an antenna of the implantable medical device, wherein the RF telemetry signal is within the predetermined frequency band for RF telemetry communication;
  modulating, by the communication transmitter module, a TCC signal;
  transmitting, by the communication transmitter module, the TCC signal to another implantable medical device implanted within the patient with the plurality of electrodes coupled to the implantable medical device, wherein the TCC signal is within the predetermined frequency band for RF telemetry communication;
  selectively coupling, by a switching module of the implantable medical device comprising one or more switches, the plurality of electrodes to either the sensing module or at least one of a communication receiver module of the implantable medical device or the communication transmitter module;

determining, by a processor of the implantable medical device, a heart rate of the patient based on depolarizations sensed by the sensing module in the cardiac electrogram;

determining, by the processor, that the heart rate is greater than a threshold value; and changing, by the processor, the switching module from a first configuration in which the antenna is coupled to the communication receiver module and the plurality of electrodes are decoupled from the communication receiver module to a second configuration in which the antenna is decoupled from the communication receiver module and the plurality of electrodes are coupled to the communication receiver module in response to the determination that the heart rate is greater than the threshold value.

19. The method of claim 18, further comprising selectively coupling, with the switching module, the communication transmitter module to either the antenna or the plurality of electrodes.

20. The method of claim 19, wherein the implantable medical device comprises an extravascular implantable cardioverter defibrillator comprising:
a therapeutic signal generator configured to deliver therapeutic shocks to a heart of the patient via the plurality of electrodes,
the method further comprising selectively coupling, with the switching module, the plurality of electrodes to at least one of the communication transmitter module, the sensing module, or the therapeutic signal generator.

21. The method of claim 20, wherein the TCC signal is transmitted to a leadless pacing device implanted within the patient and includes a command to deliver at least one of anti-tachycardia pacing (ATP) or post-shock pacing.

22. The method of claim 18, wherein the implantable medical device further comprises a therapeutic signal generator configured to deliver a therapeutic electrical signal to the patient via the at least one of the plurality of electrodes, the method further comprising selectively coupling, with the switching module, the at least one of the plurality of electrodes to at least one of the communication transmitter module, the sensing module, or the therapeutic signal generator.

23. The method of claim 18, wherein modulating the RF telemetry signal and the TCC signal comprises modulating the RF telemetry signal and the TCC signal using different modulation techniques.

24. The method of claim 18, wherein the TCC signal includes a message, and transmitting the TCC signal comprises transmitting the TCC signal including the message a plurality of times during a cardiac cycle.

25. A system comprising:
an extravascular implantable cardioverter defibrillator comprising:
a first antenna;
a first plurality of electrodes;
a first sensing module configured to receive a first cardiac electrogram of a patient via the first plurality of electrodes;
a first therapeutic signal generator configured to deliver therapeutic shocks to a heart of the patient via the first plurality of electrodes;
a communication transmitter module configured to modulate and transmit signals within a predetermined frequency band for radio-frequency (RF) telemetry communication, wherein the communication transmitter module is configured to modulate and transmit a first RF telemetry signal to an external device via the first antenna, and modulate and transmit a tissue conduction communication (TCC) signal via the first plurality of electrodes, wherein the TCC signal is within the predetermined frequency band for RF telemetry communication; and
a first switching module configured to selectively couple the first plurality of electrodes to at least one of:
the first sensing module;
the first therapeutic signal generator; or
the communication transmitter module; and
a leadless pacing device comprising:
a second antenna;
a second plurality of electrodes;
a second sensing module configured to receive a second cardiac electrogram of the patient via the second plurality of electrodes;
a second therapeutic signal generator configured to deliver cardiac pacing pulses to a heart of the patient via the second plurality of electrodes;
a communication receiver module configured to receive and demodulate signals within the predetermined frequency band for RF telemetry communication, wherein the communication receiver module is configured to receive from the second antenna and demodulate a second RF telemetry signal emitted by the external device, and receive from the second plurality of electrodes and demodulate the TCC signal emitted by the extravascular implantable cardioverter defibrillator;
a second switching module configured to selectively couple the second plurality of electrodes to at least one of:
the second sensing module;
the second therapeutic signal generator; or
the communication receiver module; and
a housing configured for implantation within the heart of the patient, wherein the housing encloses the second antenna, the communication receiver module, the second switching module, the second sensing module, and the second therapeutic signal generator, and wherein the housing comprises at least one of the second plurality of electrodes,
wherein the TCC signal includes a command from the extravascular implantable cardioverter defibrillator to the leadless pacing device to deliver at least one of anti-tachycardia pacing (ATP) or post-shock pacing, and
wherein the leadless pacing device further comprises a processor within the housing, wherein the processor is configured to:
determine a heart rate of the patient based on depolarizations sensed by the second sensing module in the second cardiac electrogram;
determine that the heart rate is greater than a threshold value; and
change the second switching module from a first configuration in which the second antenna is coupled to the communication receiver module and the second plurality of electrodes are decoupled from the communication receiver module to a second configuration in which the second antenna is decoupled from the communication receiver module and the second plurality of electrodes are coupled to the communication receiver module in response to the determination that the heart rate is greater than the threshold value.

26. The system of claim 25, wherein the leadless pacing device further comprises a processor within the housing, wherein the processor is configured to:

detect a shock delivered by the extravascular implantable cardioverter defibrillator based on the second cardiac electrogram received by the second sensing module; and change the second switching module from the first configuration in which the second antenna is coupled to the communication receiver module and the second plurality of electrodes are decoupled from the communication receiver module to the second configuration in which the second antenna is decoupled from the communication receiver module and the second plurality of electrodes are coupled to the communication receiver module in response to the detection of the shock.

27. The system of claim 25, wherein the communication transmitter module of the extravascular implantable cardioverter defibrillator is configured to send another TCC signal that includes a command to the leadless pacing device to shorten a pacing interval, wherein the communication receiver module of the leadless pacing device receives the other TCC signal, and the second therapeutic signal generator shortens the pacing interval in response to the command to shorten the pacing interval, and wherein the first sensing module of the extravascular implantable cardioverter defibrillator detects the shortened pacing interval to confirm receipt of the command.

* * * * *